(12) United States Patent
Finke et al.

(10) Patent No.: US 11,610,473 B2
(45) Date of Patent: Mar. 21, 2023

(54) CONTROL DEVICE FOR AEROSOL NEBULIZER SYSTEM

(71) Applicant: PARI Pharma GmbH, Starnberg (DE)

(72) Inventors: Matthias Finke, Munich (DE); Carola Fuchs, Neuried (DE); Björn Eschrich, Peiting (DE); Edgard Osswald, Munich (DE); Philipp Kroneberg, Olching (DE); Michael Hahn, Krailling (DE); Ingo Schraut, Ravensburg (DE); Sascha Roeder, Munich (DE)

(73) Assignee: PARI Pharma GmbH, Starnberg (DE)

( * ) Notice: Subject to any disclaimer, the term of this patent is extended or adjusted under 35 U.S.C. 154(b) by 754 days.

(21) Appl. No.: 16/493,093

(22) PCT Filed: Mar. 16, 2018

(86) PCT No.: PCT/EP2018/056682
§ 371 (c)(1),
(2) Date: Sep. 11, 2019

(87) PCT Pub. No.: WO2018/167278
PCT Pub. Date: Sep. 20, 2018

(65) Prior Publication Data
US 2020/0193806 A1 Jun. 18, 2020

(30) Foreign Application Priority Data
Mar. 17, 2017 (EP) .................... 17161545

(51) Int. Cl.
*G08B 21/04* (2006.01)
*G08C 17/02* (2006.01)
(Continued)

(52) U.S. Cl.
CPC .......... *G08C 17/02* (2013.01); *A61M 15/009* (2013.01); *A61M 15/0013* (2014.02);
(Continued)

(58) Field of Classification Search
USPC .. 340/539.12, 517, 521, 539.22, 539.3, 593, 340/588, 618, 632, 5.52, 7.32
See application file for complete search history.

(56) References Cited

U.S. PATENT DOCUMENTS 6,901,926 B2 * 6/2005 Yamamoto .......... B05B 17/0638
128/200.16
9,533,114 B1 1/2017 Kayyali et al.
(Continued)

FOREIGN PATENT DOCUMENTS

DE  102 43 371 A1  4/2004
WO  WO 2004/028606 A1  4/2004
(Continued)

OTHER PUBLICATIONS

Japanese Office Action dated Aug. 27, 2021 in connection with Japanese Application No. 2019-571790, and English translation thereof.
(Continued)

*Primary Examiner* — Daniel Previl
(74) *Attorney, Agent, or Firm* — Wolf, Greenfield & Sacks, P.C.

(57) ABSTRACT

The present invention relates to a control device for controlling an operation of an aerosol nebulizer system (30), said aerosol nebulizer system (30) comprising an aerosol generator (31) for nebulizing a liquid and a plurality of sensor units (38*a*, 38*b*, 38*c*, 38*d*, 38*e*), said control device (20) comprising: a communication unit (21), configured to establish a wireless communication connection and to perform data transmission with the aerosol nebulizer system (30), a sensor data control unit (22), configured to trigger a selection of sensor data related to the sensor units (38*a*, 38*b*, 38*c*, 38*d*, 38*e*) to be wirelessly transmitted to the control device (20).

27 Claims, 10 Drawing Sheets

(51) Int. Cl.
*A61M 15/00* (2006.01)
*G16H 40/67* (2018.01)
*G16H 20/13* (2018.01)
*G08C 23/04* (2006.01)
*H04L 67/12* (2022.01)
*A61M 16/00* (2006.01)

(52) U.S. Cl.
CPC .... *A61M 15/0018* (2014.02); *A61M 15/0021* (2014.02); *A61M 15/0086* (2013.01); *G08C 23/04* (2013.01); *G16H 20/13* (2018.01); *G16H 40/67* (2018.01); *H04L 67/12* (2013.01); *A61M 2016/0015* (2013.01); *A61M 2205/3379* (2013.01); *A61M 2205/3569* (2013.01); *A61M 2205/3584* (2013.01); *A61M 2205/3592* (2013.01); *A61M 2205/50* (2013.01); *A61M 2205/505* (2013.01); *A61M 2205/581* (2013.01); *A61M 2205/582* (2013.01); *A61M 2205/583* (2013.01); *G08C 2201/50* (2013.01); *G08C 2201/93* (2013.01)

(56) References Cited

U.S. PATENT DOCUMENTS

| | | | |
|---|---|---|---|
| 2002/0138017 A1* | 9/2002 | Bui | G16H 40/67 600/537 |
| 2004/0045547 A1* | 3/2004 | Yamamoto | B05B 17/0638 128/200.14 |
| 2006/0237001 A1 | 10/2006 | Stangl | |
| 2009/0056708 A1* | 3/2009 | Stenzler | A61M 15/002 128/200.14 |
| 2009/0063187 A1 | 3/2009 | Johnson et al. | |
| 2009/0118595 A1 | 5/2009 | Greiner et al. | |
| 2009/0178672 A1 | 7/2009 | Mullinger et al. | |
| 2011/0225008 A1 | 9/2011 | Elkouh et al. | |
| 2012/0094600 A1 | 4/2012 | Dellostritto et al. | |
| 2016/0301991 A1 | 10/2016 | Loychik et al. | |
| 2016/0325057 A1* | 11/2016 | Morrison | A61M 15/0026 |
| 2016/0346489 A1 | 12/2016 | Finke et al. | |
| 2017/0020196 A1* | 1/2017 | Cameron | A24F 40/50 |
| 2018/0264209 A1* | 9/2018 | Hazani | A61M 15/009 |
| 2020/0008299 A1* | 1/2020 | Tran | H05K 1/0386 |

FOREIGN PATENT DOCUMENTS

| | | |
|---|---|---|
| WO | WO 2005/114524 A2 | 12/2005 |
| WO | WO 2015/091356 A1 | 6/2015 |
| WO | WO 2017/137424 A1 | 8/2017 |
| WO | WO 2018/167278 A1 | 9/2018 |

OTHER PUBLICATIONS

International Search Report and Written Opinion dated Jun. 11, 2018 in connection with International Application No. PCT/EP2018/056682.

[No Author Listed], Human Respiratory Tract Model for Radiological Protection. International Commission on Radiological Protection. ICRP Publication 66. Ann. ICRP. 1994; 24(1-3):492 pages.

Hofmann et al., Monte Carlo modeling of aerosol deposition in human lungs. Part III: Comparison with experimental data. Journal of Aerosol Science. Jan. 1992; 23(1):51-63.

Isaacs et al. Modeling Deposition of Inhaled Particles. Second Edition Chapter 5, Lev S. Ruzer, Naomi H. Harley (ed.), Handbook: Measurement, Dosimetry, and Health Effects. 2012;83-127.

Koblinger et al., Analysis of human lung morphometric data for stochastic aerosol deposition calculations. Physics in Medicine and Biology. Jun. 1985; 30(6):541-556.

* cited by examiner

CONTROL DEVICE FOR AEROSOL NEBULIZER SYSTEM

RELATED APPLICATIONS

This Application is a national stage filing under 35 U.S.C. § 371 of International Patent Application No. PCT/EP2018/056682, filed Mar. 16, 2018, which claims the benefit of European application number EP 17161545.3, filed Mar. 17, 2017. The entire contents of these applications are incorporated herein by reference in their entirety.

TECHNICAL FIELD

The present invention relates to a control device for controlling an operation of an aerosol nebulizer system, which may also be used for controlling a spirometer system and/or a respiratory gas analysis system.

BACKGROUND

Conventional aerosol nebulizers are known to have an aerosol generator to generate an aerosol from a liquid medication. To improve the usability of the aerosol nebulizers for the user/patient, an external control device may be used. Such a control device, for example a smartphone implementing an application software program (an APP or a mobile APP), may comprise a processor, a memory, for example in the form of a non-volatile memory, a display, and an input unit which may be configured in the form of a keyboard, individual buttons, or a touch-sensitive surface in the display.

Such an external control device may additionally implement a suitable interface to establish a wireless communication connection with the aerosol nebulizer to transfer configuration data to the aerosol nebulizer to appropriately set and control the operation of the aerosol generator. Similarly, nebulization data and/or measurement data (also referred to as therapy-related data) may be generated by one or more sensor units of the aerosol nebulizer and may be transferred from the aerosol nebulizer to the external control device via the wireless communication connection. Such nebulization data and/or measurement data may, for example, be generated by an internal control unit of the aerosol nebulizer or the one or more sensor units that are mounted at the aerosol nebulizer and/or are connected with the aerosol nebulizer. An example of such an external control device is an external computing device, for example in the form of a smartphone or a PDA as described in DE 102 43 371 A1 or US 2006/0237001 A1.

Such an external control device may further exhibit a telecommunication module and may thus further offer the capability to transfer the configuration data and inhalation/measurement data (sensor data) via the internet or a cloud to a central data base or a central data server, for example for telemedicine purposes and for the purpose of (centralized) electronic health records, or to an individual recipient other than the user itself, for example to the physician of the patient.

SUMMARY OF THE INVENTION

Technical Problem

In order to improve the medical success of the inhalation therapy by improving adherence to a therapy protocol, by dynamically adapting the therapy protocol, and by providing real-time therapy-related functionality, such as patient training and support at the control device during the inhalation process, it has been further proposed to connect the above external control device to a diagnostic device to monitor a state of the respiratory tract and/or a state and/or function of the lung of the user/patient. An example of such a diagnosis device is a flow-sensor or especially a spirometer that is able to measure the air flow rate and volume inhaled/exhaled by the lungs of the user/patient. Further, a spirometer may measure ventilation, i.e. the movement of air into and out of the lungs. As known, there are various types of spirometers which use a number of different sensor units for measurement, for example a pressure transducers, an ultrasonic transmitter, a hot-wire anemometer, a turbine (optical, acoustic) which also generate therapy-related data, in particular diagnostic-related data.

As such, the plurality of sensor units mounted at or connected with the aerosol nebulizer and/or the plurality of additional sensor units mounted at or connected with the spirometer all generate sensor data to be transmitted by using a wireless communication connection with the external control device. For example, in DE 102 43 371 A1 and US 2006/0237001 A1 it is proposed to continuously supply measuring signals of sensor units as long as the aerosol nebulizer is switched on and to continuously transmit all therapy-related data derived by processing the continuously supplied measuring signals. The data transmission rate, i.e. the amount of data per unit time that may be transmitted via the established wireless communication connection may, however, be fixed. In particular, this may be the case when a low capacity wireless communication connection is used, such as Bluetooth Low Energy, for example for the purpose of limiting battery requirements of the portable aerosol nebulizer and/or spirometer. As the amount of sensor data continues to increase due to the application of additional sensor units, a fixed data transmission rate may be detrimental to providing real-time therapy-related feedback functionality, such as patient training and support at the control device during the process of inhalation and/or spirometer use.

Against this background, it is an objective of the present invention to provide a control device that overcomes the above described technical disadvantages.

Solution

The features of a control device according to the present invention are defined in claim 1. Advantageous embodiments are described in the dependent claims.

Further, the features of a computer program according to the present invention are defined in claim 25, while the features of a computer-readable storage medium and a carrier containing the computer program are defined in claims 26 and 27, respectively.

DESCRIPTION OF THE EMBODIMENTS

Embodiments of the present invention are described with reference to the Figures. It is noted that the following description should not be construed as limiting the invention. In the following, similar or same reference signs indicate similar or same elements or operations.

Figure 1:
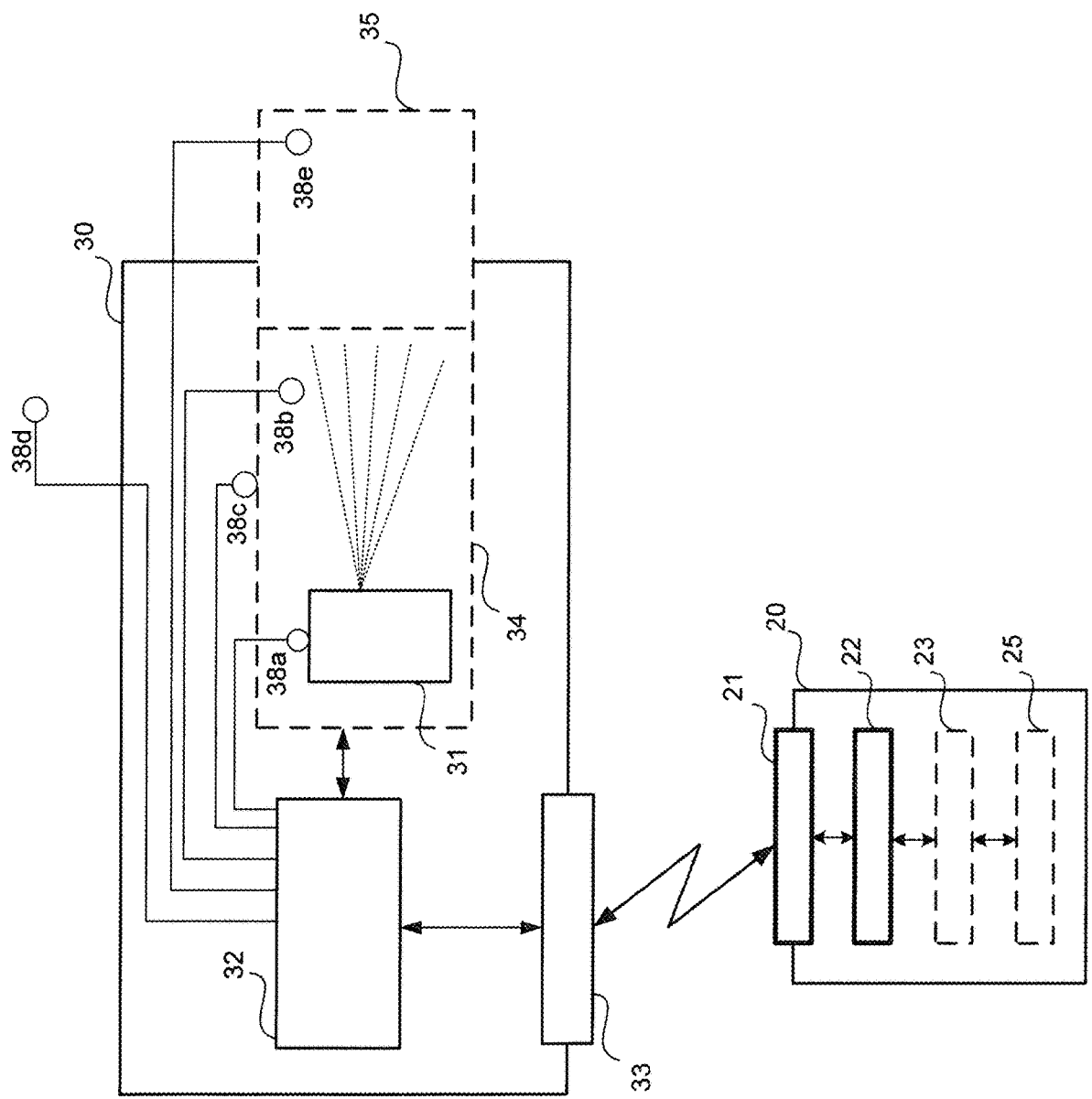
FIG. 1 shows a schematic illustration of a control device for an aerosol nebulizer system according to an embodiment.

FIG. 1 shows a control device 20 according to an embodiment in combination and communication interaction with an aerosol nebulizer system 30.

Here, the aerosol nebulizer system 30 may comprise an aerosol generator 31, for example a membrane aerosol generator or the like, that is suitable to nebulize a liquid, which is held in a reservoir 78 of the aerosol nebulizer system 30. The liquid may be a fluid that contains at least one active pharmaceutical ingredient, medical drug and/or at least one therapy relevant fluid (such as a sodium chloride solution), and/or a fluid from which an aerosol is generated for the purpose of assisted diagnosis (such as a fluorescent aerosol, a mono-disperse aerosol, or the like). The liquid/fluid is transformed into an aerosol by the aerosol generator 31, which subsequently enters e.g. a mixing chamber 34 that is connected to a mouthpiece 35. From the mouthpiece, the patient/user inhales the aerosol into the respiratory tract, like lung, throat, nose or sinuses, to perform a medical treatment according to a prescribed aerosol therapy protocol. Further, the aerosol generator 31 (FIG. 1) operates according to configuration data that may be provided from the control device 20 via a communication interface 33 or may be pre-set at a processing unit 32 of the aerosol nebulizer system 30. Conversely, the aerosol nebulizer system 30 provides inhalation data and/or measurement data (also referred to as therapy-related data or sensor data in the following) generated by one or more sensor units 38a, 38b, 38c, 38d, 38e at or near the aerosol nebulizer system 30 via the established wireless communication interaction to the control device 20. Here, the wireless communication connection may be one of a Bluetooth connection, a Bluetooth Low Energy connection, a near field connection, a WiFi or WLAN connection, an infrared connection, a LoRa connection (a low power wide area network connection intended for wireless battery operated Internet of things devices), a radio connection, or the like. Here, the data rate of Bluetooth Low Energy, for example, may be lower than 200 kBit/s, or even lower than 100 kBit/s. In addition, a wireless LoRa connection may have a data rate as low as 0.3-50 kBit/s. Further, the configuration data and/or the sensor data may be encrypted to avoid unauthorized access. In addition, data integrity may be guaranteed at all times by implementing an error correction functionality (based on checksums, or the like).

In the embodiment shown in FIG. 1, the aerosol nebulizer system 30 comprises five sensor units 38a, 38b, 38c, 38d, 38e but the aerosol nebulizer system 30 is not limited to these five sensor units and may comprise more or less sensor units. In general, the sensor units supply measuring signals of parameters relevant for the therapy to the processing unit 32 which generates therapy-related data from said measuring signals by means of a signal-based processing (e.g. analog-digital conversion, filtering, amplification) of the measuring signals. The therapy-related data (sensor data) is released to the communication interface 33 by the processing unit 32 so as to be wirelessly transmitted to the control device 20.

The sensor units 38a, 38b, 38c, 38d, and 38e shown in FIG. 1 represent examples of different sensor units which generate measuring signals. For example, sensor unit 38a may detect the operation state of the membrane aerosol generator 31, for example the power consumption, temperature and/or current output and/or consumption of aerosol, the filling status of the liquid reservoir or another therapy-relevant parameter of the aerosol generator 31. The operation state of the membrane aerosol generator and/or the therapy-relevant parameter may be measured or calculated directly or indirectly from the sensor signals. The sensor unit 38b may detect the presence of aerosol and the aerosol density in the mixing chamber 34. The sensor unit 38c may be an environmental condition sensor unit to detect, for example, the temperature, humidity, pollution of ambient air and/or the pressure of the ambient air. Further, sensor unit 38d may detect, for example, the respiratory flow of the patient. Such a breathing maneuver sensor unit may determine a breathing (exhaling and inhaling) maneuver and a respiratory flow of the user/patient during inhalation of the generated aerosol and during exhalation. In addition, sensor unit 38e may detect an actual contact of the user/patient with the mouthpiece 35. Of course the mouthpiece 35 could be any kind of an interface, like for example a mouthpiece, a face mask, a nasal prongs, a tube as well as each contact area to detect an actual contact of the user/patient like for example a contact surface, a display, a button, a handle and so on.

Although five sensor units 38a, 38b, 38c, 38d and 38e are shown in the embodiment according to FIG. 1, it is obvious that an aerosol nebulizer system 30 according to the invention can be equipped with more or less sensor units for generating more or less therapy-relevant measuring signals.

For example, an aerosol sensor unit may further determine one or more parameters of the generated aerosol such as aerosol density, aerosol quality, for example a statistical property of the aerosol droplets such as a mass median diameter (MMD), a mass median aerodynamic diameter (MMAD), a standard deviation from the MMD or MMAD, GSD (geometric standard deviation) or the like.

Further, a user recognition sensor unit may be provided to identify the current user of the aerosol nebulizer. As will be further discussed below, user recognition may be based on a code, icon, a smartcard, facial recognition, fingerprint, iris scan, and/or special features of the sensor units. In addition, the user recognition may also be achieved via receiving identification data from the present control device, receiving identification data based on an app, or receiving identification data from an external device, such as a medical device (hearing aid device, cardiac pacemaker, an insulin pump) or vehicle which itself is provided with a capability to scan and recognize a user.

In addition, an aerosol generator identification sensor unit may identify a specific type of aerosol generator currently used at the aerosol nebulizer system, and a medication identification sensor unit to identify the type of medication that is currently used when generating aerosol. This identification may be based on an optical spectral measurement (within the liquid or within the aerosol droplets) or may be based on an RFID chip or another storage element being provided on an ampule containing the liquid, an electrical resistance measurement within the fluid, or the like.

In addition, an aerosol nebulizer battery sensor unit may be provided in order to determine a current state of charge (SOC), of a battery, previous charging and/or discharging cycles, a battery voltage of the battery, respective battery voltages of battery cells, and the like. This may be achieved by measuring a cell voltage, a charging and/or discharging current, a charging and/or discharging time, and a comparison with respective target values which may be provided in a lookup table. In addition, when inserting a new battery cell, the new electric parameters (voltage, current, SOC) may be compared with such target values.

The external control device 20 according to FIG. 1 may be a smartphone, a tablet, a personal digital assistant (PDA), a netbook, a notebook, a laptop, a personal computer, a wearable device such as a smart watch, a smart glasses, a running computer, hearing aid device, implanted medical device, like an insulin pump computer or another portable device.

The control device 20 of the aerosol nebulizer system 30 according to an embodiment may be equipped with an application program (e.g. an APP) for therapy-related evaluation. The program may be stored in a memory unit 25 of the control device 20 and may be started from there within the framework of the operating system of the control device 20. Furthermore, it is alternatively possible to transfer an application program into the memory unit 25 of the control device 20 via an interface, for example the communication unit 21 or an additional interface (RS-232, USB, FireWire, or the like) and to start it from there within the framework of the operating system of the control device 20. Finally, such an application program may be loaded into the memory unit 25 of the control device 20 via a remote data connection unit (not shown), for example downloaded via the Internet, and may be started from there within the framework of the operating system of the control device 20.

Conventionally, following switching on of the aerosol nebulizer system 30, the sensor units 38*a*, 38*b*, 38*c*, 38*d*, and 38*e* generate sensor signals for the processing unit 32, which generates therapy-related data (sensor data) from the measuring signals by means of a signal-based processing of said measuring signals and conveys the sensor data to the communication interface 33. The communication interface 33 will transmit the sensor data to the communication unit 21 of the external control device 20 as long as the sensor data are received from the processing unit 32. Such a continuous generation of sensor data from a plurality of sensor units may thus lead to a transmission bottleneck because the amount of sensor data that may be transmitted per unit time via the established wireless communication connection between the aerosol nebulizer system 30 and the external control device 20 may be limited. In particular, this may be the case when a (fixed) low capacity wireless communication connection is used, such as Bluetooth Low Energy, for example for the purpose of limiting battery requirements of the portable aerosol nebulizer. However, a limited data transmission rate may be detrimental to providing a real-time therapy-related functionality at the control device 20, such as patient training and support at the control device. For example, such a real-time feedback function at the control device may implement a simulation and/or animation module which provides visual and/or audio feedback to guide the user through the therapy application and/or appropriately corrects the therapy application. In one embodiment such a visual feedback may be provided using a visual representation on data glasses, smart glasses, virtual reality glasses or the like which may support the real-time guidance through the therapy, training, exercise course, application, and diagnostic protocol and potential correction with a minimal interference of the actual usage of the aerosol nebulizer system 30 (and/or the spirometer system and/or the respiratory gas analysis system to be described below).

To overcome the above technical limitations, the control device 20 according to FIG. 1 is provided with a sensor data control unit 22. The sensor data control unit 22 may trigger a selection of sensor data, e.g. an appropriate sub-set of currently generated sensor data, which should be wirelessly transmitted from the communication interface 33 of the aerosol nebulizer system 30 to the communication unit 21 of the control device 20. Here, the selection of currently generated sensor data from the sensor data control unit 22 at the aerosol nebulizer system 30 may be triggered by transmitting a corresponding signaling (indication) or the like.

Figure 2:
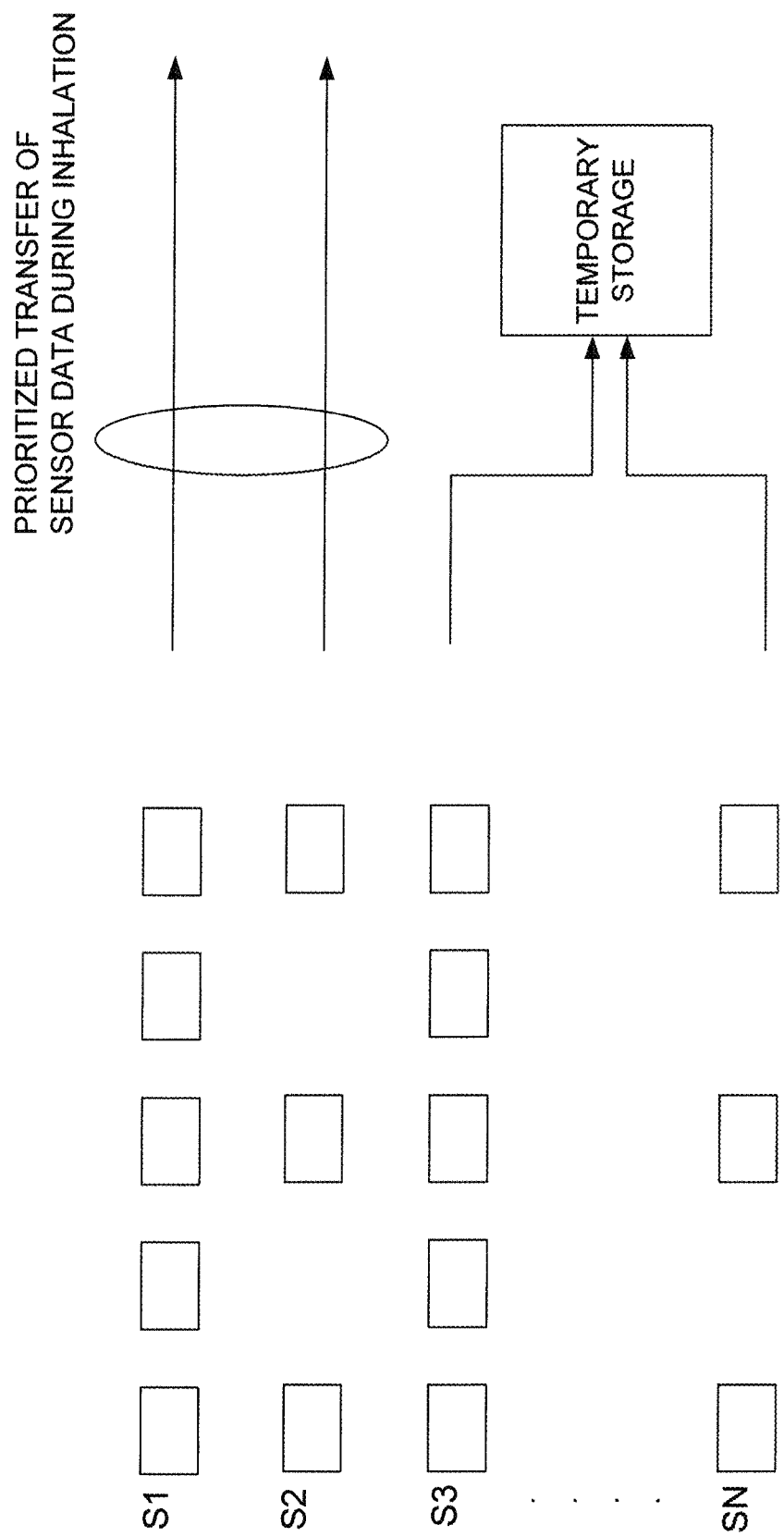
FIG. 2 shows a schematic illustration of prioritizing sensor data transmission during inhalation.
Figure 3:
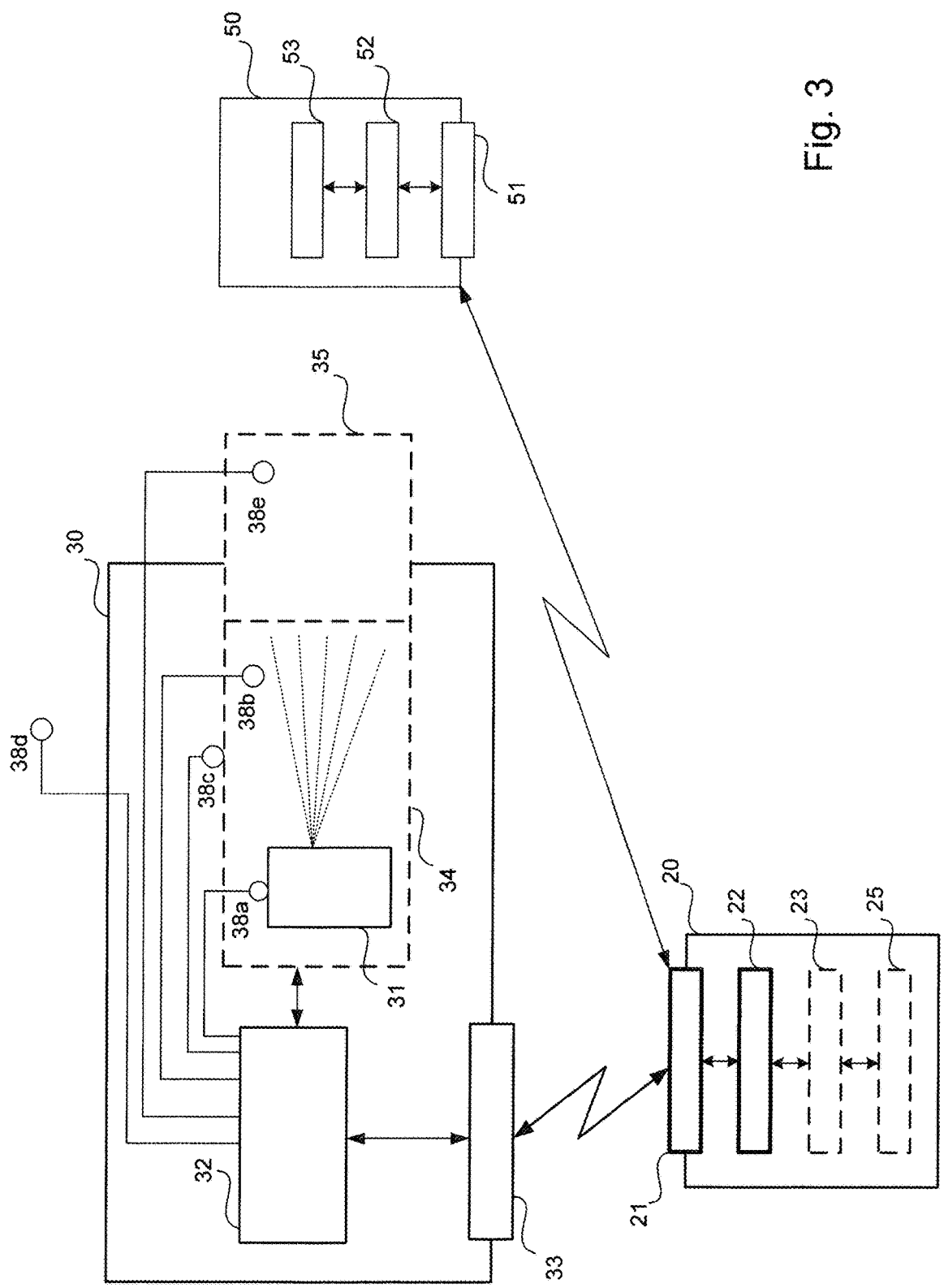
FIG. 3 shows a schematic illustration of a control device for an aerosol nebulizer system and a spirometer system according to an embodiment.
Figure 4:
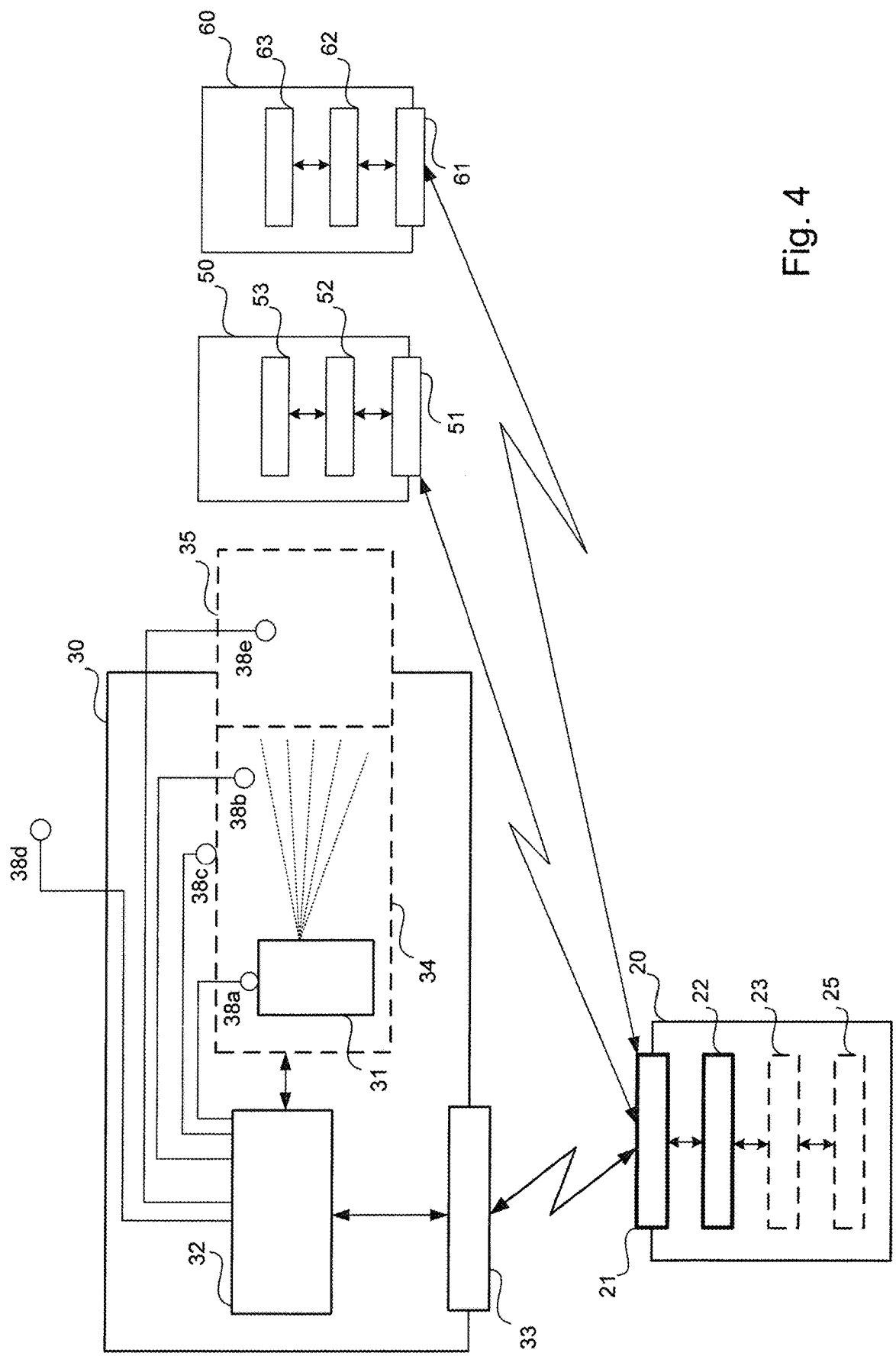
FIG. 4 shows a schematic illustration of a control device for an aerosol nebulizer system, a spirometer system, and a respiratory gas analysis system according to an embodiment.

FIG. 2 illustrates this approach on the basis of sensor units S1, S2, . . . , SN which give rise to respective sensor data (illustrated as boxes in FIG. 2) which may be continuously generated with the same frequency or different frequencies. For example, each of the sensor units may generate, in part, more than 1,000 measurement values (to be transferred into sensor data). During inhalation, only selected and prioritized sensor data are transmitted to the control device. The sensor data may be reduced for example via a look up table (data base), logic, and/or algorithm, like sample values, average values, trend analyses, and/or curve sketching. This concept is further illustrated in FIG. 2. In particular, a sub-set of sensor data (here, the sensor data corresponding to sensor S1 and S2) are subjected to a prioritized transfer to the external control device 20 during inhalation, while the remaining sensor data (here, the sensor data corresponding to sensor S3 and SN) are temporarily stored at the aerosol nebulizer system for a subsequent transfer, for example after the inhalation. In particular, during the inhalation process, the control device 20 may thus provide a real-time feedback based on the prioritized transfer of a sub-set of sensor data that are required for this real-time feedback.

Here, the feedback may be provided as a video, a visual explanation or acoustic tutorial and may include a personal training, a training program, a personal teacher, a physiotherapist or the like. This may include a bonus or credit system in combination with the caregiver, physician, or pharmacist, clinic research organization (CRO), manufacturer, Pharmaceutics Company and so on.

For example, when the user/patient starts the inhalation process, the aerosol nebulizer system may send a corresponding message to the control device 20 which switches into an inhalation mode. This inhalation mode may involve a specific inhalation training or an application supporting the inhalation in real time based on the transmitted sensor data. On the other hand, this inhalation mode may involve also a specific gamification mode (including animations, for example for children) which may only be displayed (or played) during inhalation. Here, a gamification bonus system may additionally increase a therapy adherence.

Starting the inhalation process may also activate additional sensor units, for example with regard to a respiratory flow measurement, an aerosol density measurement, a particle size measurement, a use measurement, a touch measurement, a tilt measurement, and/or the accelerator measurement. If sensor data of such sensors exceed or fall below a predefined or adapted threshold, a warning indication may be indicated both at the aerosol nebulizer system 30 and the control device 20. In addition, if the tilting angle of the aerosol nebulizer system 30 exceeds a predefined or adapted threshold, then the real-time simulation, animation and/or game (gamification) is interrupted and a corresponding indication is displayed at the control device that guides the user/patient back to a proper inhalation process.

The above inhalation modes may also be defined with regard to different users of the control device 20 and the aerosol nebulizer system 30. In one mode, a child is using the aerosol nebulizer system 30 while a parent/caregiver/supervisor is provided at the control device 20 with a detailed real-time feedback (push notification) that may further include a full deposition simulation and/or an inhalation evaluation (like a light signal: green, yellow, red), for example. The parent/caregiver/supervisor may thus determine whether the inhalation is performed properly. In another mode, the child also uses the control device and is playing a game (as described above), e. g. interactively animated by individual use(s) of the aerosol nebulizer system (30), while the control device collects the transmitted sensor data. The distinction between the different modes may be based on a user recognition at both the control device 20, and the aerosol nebulizer system 30, as will be further described below.

In addition, the control device 20 may also trigger a selection of sensor data based on defined thresholds, which may also be appropriately adapted during the course of the therapy protocol, for example when the health state of the user improves or deteriorates. Here, such thresholds may be transmitted to the aerosol nebulizer system 30 in the form of configuration data or as an explicit signaling.

For example, the sensor data of an accelerometer and/or a tilt sensor are only transmitted when no movement of the aerosol nebulizer system has been detected for a certain time period or a previously defined threshold for a tilt angle, as provided by the control device 20, is exceeded.

According to a further example, the control device 20 may trigger a transfer of only a sub-set of all the sensor data of a particular sensor unit. For example, of all the sensor data of a respiratory flow sensor, only every $n^{th}$ (n>1) sensor data are transmitted, as long as only a qualitative evaluation of the breathing maneuver at the display of the control device is required, and not a complete spirometry measurement. An entire measurement curve (for example, the entire measurement curve with regard to spirometry, as described below) and/or one or more respiratory cycles during the inhalation may then afterwards be acquired from the temporary storage and transmitted to the control device 20.

According to a further example, the sensor data of an aerosol density sensor will only be transmitted to the control device 20 if the aerosol density changes significantly, for example by more than a specific threshold.

As another example, the sensor unit 38*a* for detecting the presence of a liquid/fluid in contact with the membrane of the aerosol generator and/or in the reservoir on the basis of a statistical data analysis (e.g., slopes of data curves and/or area under data curves) of electrical parameter(s) and a vibration frequency, such as described in WO 2015/091356 A1, may be configured to provide corresponding sensor data to the control device only when the reservoir is empty or no liquid/fluid is provided at the membrane, for example when the tilt angle exceeds such a threshold.

Based on the above two examples, also an improved deactivation of the aerosol generator may be achieved on the basis of the accelerometer and/or the tilt sensor, the sensor unit 38*a* for detecting the presence of a liquid/fluid, and the sensor unit 38*b* for detecting aerosol density and/or aerosol quality. In particular, based on the accelerometer or preferably the tilt sensor data, it may be determined whether the liquid reservoir is indeed empty, or whether the liquid is not in contact with the membrane only because the tilt angle is too large (exceeds a particular threshold). In the latter case, the aerosol generator is not deactivated and the user is informed in real-time to appropriately hold the aerosol nebulizer system upright.

Here, a priority table may be provided by the sensor data control unit 22. Such a priority table may define which sensor data are to be transmitted "live" during a specific operation of the aerosol nebulizer system. For example, such a priority table may define that only a reduced set of sensor data is transmitted during a normal inhalation (e.g. if the respiratory flow is larger than a defined threshold) while the remaining sensor data of the remaining sensor units are transmitted only outside a defined transmission window (for "live" transmission). During a training inhalation mode, on the other hand, in order to learn a proper breathing maneuver, the priority table may define to transmit more sensor data of the respiratory flow sensor which are graphically displayed as shown in FIG. 5D, for example in conjunction with a deposition simulation, an inhalation evaluation, and/or a success rate indicator, at a display unit of the control device 20 in order to provide a real-time feedback.

The sensor data control unit 22 may thus signal to the aerosol nebulizer system 30 that a real-time feedback functionality is performed at the control unit 20. Responsive to such an indication, the aerosol nebulizer system 30 does not attempt to transmit the entire amount of sensor data currently generated at the processing unit 32, but performs an operation to transmit only a sub-set of the currently generated sensor data, in particular the sensor data which are required for executing the real-time feedback at the control device. In other words, the selection of appropriate sensor data may be achieved by filtering out or selecting an appropriate sub-set of sensor data which is required with a higher priority at the control device. That is, the sensor data which have been or will be generated by the (above described) processing unit 32 are prioritized so that a sub-set of sensor data is released for transmission to the control device, for example for the purpose of providing a real-time feedback. The remaining set of sensor data, which is not immediately required at the control device, may be temporarily stored (cached or buffered) in the aerosol nebulizer system 30, and may be transmitted to the control device 20 at a later time point, for example when the real-time feedback is not executed any more, or according to a designated pull operation by the control device at a later point in time. In another preferred embodiment, the remaining set of sensor data may only be transmitted when a particular data transfer capability, such as a WiFi connection or a LoRa connection can be established, for example when the user is in a particular location.

For example, the evaluation unit 23, as shown by dashed lines in FIG. 1, may determine an actual breathing (exhaling and inhaling) maneuver (also referred to as a breathing pattern in the following) of the patient during inhalation of the generated aerosol based on data generated by the breathing maneuver sensor unit. Based on a predetermined and stored optimal breathing maneuver, the evaluation unit 23 may generate an indication and/or warning to the patient/user if the actual breathing maneuver deviates from the optimal breathing maneuver with respect to one or more predetermined threshold values. Here, the optimal breathing maneuver may be determined by the control device 20 based on patient/user information such as age, gender, medical indication, lung function, size and weight, severity of the illness, and the like, which may subsequently be adapted by the medical doctor. Such an optimal breathing maneuver may be characterized by a set of key variables such as a recommended breathing rate [1/min], peak inspiratory flow rate and/or average inspiratory flow rate [Liter/min], inspiratory volume [Liter], inhalation period [sec], inhalation/exhalation period ratio, breath hold period [sec], the scatter (e. g. standard deviation) of any of the above variables throughout repeated breathing maneuvers, and one or more tolerance values in relation to a predefined reference value of such optimal breathing maneuver, such as for example a target peak inspiratory flow of 30 Liter/min with a tolerance range of ±10 Liter/min, preferred 20 Liter/min±7 Liter/min, and more preferred 15 Liter/min±5 Liter/min, and even more preferred 12 L/min±5 Liter/min, which may be derived for example from American Thorax Society (ATS), European Respiratory Society (ERS), the International Society for Aerosols in Medicine (ISAM), and the Global Initiative for Asthma (GINA) guidelines.

Further, by using the data generated by the breathing maneuver sensor unit during usage of the aerosol nebulizer system in connection with information as to a currently used liquid as well as the used dosage, the evaluation unit 23 may further be configured to provide a real-time (during inhalation, but also during spirometer use or during respiratory gas analysis use, as described below) estimate of a delivered dose and a real-time estimate of a total or regional aerosol deposition in the lungs, i.e. an identification of a current deposition of the aerosol in the lungs of the patient/user. This could then be used to give the patient a feedback on the successful therapy or success rate, which could be provided by displaying a deposition simulation or success rate indication on a display of the control device 20, or may be provided by an audible, visible, and/or tactile signal on the nebulizer device or on the control device.

According to a preferred embodiment, the control device 20 may execute a plurality of different real-time feedbacks. Such a feedback may be provided with regard to a handling of the aerosol nebulizer system by the user/patient. Such a feedback may also provide a failure diagnosis (for example in the form of screenshots) as to the presence of fluid, the continuation of inhalation by the user/patient, and/or as to the amount of delivered aerosol dose. Another real-time feedback example may provide an inhalation simulation and may therefore require a sub-set of sensor data as to aerosol density, aerosol quality, breathing pattern, type of medication for such a real-time feedback. On the other hand, other sensor data may not be immediately needed. For example, sensor data as to the duration of nebulization, or the positive fluid presence sensor detection may not be needed during the nebulization. Further, the ongoing sensor data as to presence of fluid at the aerosol generator may not be needed as long as sufficient medication is available in the fluid reservoir and a certain limiting threshold is not reached. In addition, sensor data as to a tilting angle only have to be transmitted when a certain critical threshold (e. g. indicating incorrect handling of the aerosol nebulizer system or indicating a particular health state (e.g. tremor, trembling, after Salbutamol inhalation, or blood oxygen (optically measured at the mouthpiece 35 for example) is reached).

As such, a plurality of different triggers (indicators) may be used by the sensor data control unit 22 to request respective different sub-sets of sensor data which should be transmitted to the control device with high priority.

According to another embodiment, the sensor data control unit 22 may be further configured to control an operation mode of one or more of the sensor units of the aerosol nebulizer system 30. Here, the operation mode may refer to a power-on mode or sleep mode of a sensor unit, to different electric power consumption stages, to a variety of different modes of generating sensor data, and/or thresholds based on which sensor data are transmitted or should not be transmitted to the control device 20 anymore. As such, the control device may selectively switch-off sensor units. The operation mode may also refer to a particular order in which the sensor data are generated and transmitted.

Here, the trigger selection and/or the operation mode in connection with defining appropriate thresholds may be based on statistical values (e.g. average values) which may be adapted or modified, if necessary.

For example, if the evaluation unit 23 of the control device determines that a tremor movement of a user (based on amplitude or frequency, as detected by an accelerometer of the aerosol nebulizer system 30) is a usual condition (average value) of the user/patient and thus does not indicate a sudden deterioration of the health status, then a suitably updated threshold may be signaled to the processing unit 32 in order to switch off the operation mode of the accelerometer or to not transmit corresponding sensor data. As such, the external control unit 20 may trigger to suspend acquiring measuring signals (and therefore generating sensor data) for a specific time period that may be set by the evaluation unit 23. Here, the power mode switching as triggered by the control device 20 may also implement a priority operation sequence of the sensor units at the aerosol nebulizer system, for example by prioritizing a subset of sensor units to provide measuring signals, which are required for a real-time feedback, with a higher sampling rate or a higher sampling accuracy.

The operation mode of the sensor units, which is controllable by the external control device 20, may thus include a data mode switching. This data mode switching may include a selective switching of the processing of measurement signals and/or the generation of sensor data on and off, so that sensor data relevant for the real-time feedback are generated with higher priority. This may also include to not immediately transmit a part of the generated sensor data via the established wireless connection, which instead may be cached or buffered at the aerosol nebulizer system. The data mode switching may also include an adaptation to the therapy protocol, for example when an updated therapy protocol for the user/patient requires addition sensor data from a sensor unit which is otherwise switched-off, for example for power-saving reasons.

Here, a patient-specific therapy protocol may be acquired by the control device 20 from an external server which is accessible by a medical doctor. The designation of such a patient-specific therapy protocol may be used by the evaluation unit to determine an adherence based on the data as transmitted by the sensor units of the aerosol generation system and also the spirometer system and respiratory gas analysis system, respectively, to be described below. Here, when the evaluation unit 23 determines a deviation from the patient-specific therapy protocol by more than pre-determined thresholds (e.g. the patient has missed a certain number of aerosol inhalations within a certain period of time, the patient has missed a certain number of spirometer usages to acquire lung diagnostic data, or the like), appropriate indications or reminders may be generated by the evaluation unit (to implement a calendar function as to when an inhalation and/or a spirometer-based measurement should be performed), or a corresponding notification may be sent to the medical doctor/supervision/caregiver/service telephone hot line/CRO or the central server which stores the patient-specific therapy protocol.

The acquired adherence data (sensor data) may thus be centrally collected, for example via a cloud solution, in one or more data bases related to a (centralized) patient record, preferably in a way in which the user/patient retains control over the adherence data and it is the user/patient which decides access properties (access time, access rights). Otherwise, standard therapy protocols may be stored in advance in the control device 20, so that the patient/user may select an appropriate standard therapy protocol based on key parameters such as age, gender, weight, size, medical indication, lung function, severity of the illness, and the like.

The sensor units of the aerosol nebulizer system 30 may thus be controlled by the external control device 20. More specifically, the operation mode of the sensor units may be controlled to selectively switch off the generation of measurement signals, although the aerosol nebulizer is switched on. In addition, the operation mode of a processing unit of the aerosol nebulizer system may be set so that the measurement signals, for example of a subset of the sensor units, are processed to generate therapy-related data, but only the therapy-related data necessary for a real-time evaluation at the external control device are transmitted to the external control device. By contrast, the part of therapy-related data not necessary for a real-time evaluation at the external control device 20 are temporarily stored at the aerosol nebulizer system, and may be acquired later by the external control device, for example based on a pull instruction from the external control device or a push instruction of the processing unit 32 in case the therapy-related data necessary for a real-time evaluation have been successfully transmitted. The start of this subsequent sensor data transfer may be delayed by a specific time interval (for example 30 seconds or 60 seconds) after the end of the real-time evaluation, a stop of aerosol generation, or the like.

Here, the evaluation unit 23 may also interact with one or more data bases (storing patient records, medical charts, and the like) or with other application programs (apps) of the control device 20, for example for the purpose of evaluating the adherence to a therapy protocol and/or an adaption of the therapy protocol in association with other health-related data such as heart rate, blood pressure, insulin levels, and the like.

FIG. 3 shows a control device 20 according to another embodiment in combination and communication interaction with an aerosol nebulizer system 30 and a spirometer system 50. FIG. 4 shows a control device 20 according to another embodiment in combination and communication interaction with an aerosol nebulizer system 30, a spirometer system 50, and a respiratory gas analysis system 60. It is noted that the respiratory gas analysis system may alternatively also be provided with the spirometer system 50, i.e. the spirometer system 50 may be capable of analyzing/evaluating the exhaled gas of the user/patient. For example the exhaled gas may be analyzed for NO, oxygen ($O_2$), an inflammation marker and so on.

In a further embodiment the spirometer system may alternatively also be provided as an integral part of the aerosol nebulizer system 30 comprising, e.g., a membrane nebulizer, a jet nebulizer, and the like. In such an embodiment the aerosol nebulizer system may also be capable of measuring the air volume inhaled/exhaled by the lungs of the user/patient, and measuring ventilation, as described above.

In a further embodiment the respiratory gas analysis system may alternatively also be provided as an integral part of the aerosol nebulizer system 30 comprising, e.g., a membrane nebulizer, a jet nebulizer, and the like. In such an embodiment the aerosol nebulizer system may also be capable of analyzing/evaluating the respiratory gas of the user/patient, as described above.

According to FIG. 3, the spirometer system 50 may comprise a plurality of additional sensor units 53 each generating measuring signals which are processed (as explained above) at the processing unit 52 to generate additional sensor data (spirometer sensor data) which may be transmitted by a communication interface 51 via an established wireless communication connection to the communication unit 21 of the control device 20.

Likewise, the respiratory gas analysis system 60 in FIG. 4 may comprise a plurality of additional sensor units 63 each generating measuring signals which are processed (as explained above) at the processing unit 62 to generate additional sensor data (respiratory gas analysis sensor data) which may be transmitted by a communication interface 61 via an established wireless communication connection to the communication unit 21 of the control device 20.

In a case where the respiratory gas analysis system is incorporated into the spirometer system, then the additional sensor units 63 of the respiratory gas analysis system would transfer respective measuring signals to the processing unit 52.

In order to appropriately perform a wireless communication process between the respective communication interfaces 33, 51, and 61 and the communication unit 21 of the control device 20, a suitable data structure should be used. Here, a data structure may be used which includes a qualifier for identifying the recipient of the data notification, i.e. control device 20, nebulizer system 30, spirometer system 50, or respiratory gas analysis system 60. In addition, the data structure may include an identifier of a data format and an identifier of a version of the data format, in order to properly evaluate the data notification, which is also flexible enough so that the data structure may be adapted and expanded for additional applications.

The spirometer system 50 and/or the respiratory gas analysis system 60 may thus be provided with one or more additional sensor units. In particular, at least one of a lung diagnostic sensor unit, a breathing gas sensor unit, a battery sensor unit, and a user recognition sensor unit may be provided. Here, the lung diagnostic sensor unit may determine a lung function based on FeV1, VC, MEF, and the like as will be further described below. Further, the breathing gas sensor unit may determine a composition of the breathing gas, such as FeNO, $NO_x$, $CO_2$, CO, $O_2$, $O_3$, VO, and the like as will be further described below. Further, the battery sensor unit may be provided in order to determine a state of charge and the like (as described above) at the spirometer system 50 and/or the respiratory gas analysis system 60. Further, also the user recognition sensor unit with a functionality as described above may be provided at the spirometer system 50 and/or the respiratory gas analysis system 60.

More specifically, a spirometer sensor unit may measure the air volume inhaled/exhaled by the lungs of the user/patient. Further, another spirometer sensor unit may measure a ventilation, i.e. the movement of air into and out of the lungs. As known, there are various types of spirometers which use a number of different methods for measurement, for example pressure transducers, ultrasonic transmitters, hot wire anemometer, or the like. Alternatively or additionally, the spirometer system 50 may have sensor unit(s) for acquiring non-respiratory parameters (i.e. systemic parameters).

Here, the evaluation unit 23 of the control device 20 may further be adapted to evaluate the adherence to the prescribed therapy protocol when additionally using the spirometer system 50 to monitor the state of the respiratory tract and/or the state and/or function of the lung of the patient. Here, the spirometer system 50 may also be used according to the prescribed therapy protocol. For example, the therapy protocol may indicate a point in time, at which a diagnosis using the spirometer system 50 should be performed. Examples of such a prescribed setting may be specific dates and/or times during the time period defined in the therapy protocol, performing the diagnosis respectively after a defined number of inhalations, such as after every five inhalations, or the like. Specific times, such as a particular number per day, week, and/or month may further depend on a specific disease (when, for example, $NO_x$ and/or cortisol values are required for asthma patients, COPD patients, or the like).

Further, the sensor data control unit 22 of the control device 20 may be configured to generate second configuration data for the spirometer system 50 and/or the respiratory gas analysis system 60. The second configuration data are data to appropriately set and control the operation of the spirometer system 50 and/or the respiratory gas analysis system 60, in particular configuration as to an operation mode of the plurality of additional sensor units mounted at and/or connected with the spirometer system 50 and/or the respiratory gas analysis system 60, respectively. The operation of the spirometer system 50 and/or the respiratory gas analysis system 60 may further be set by the second configuration data according to the prescribed therapy protocol, as described above.

For example, the second configuration data may comprise configuration data with regard to at least one of respiratory values and additional non-respiratory values (e.g. systemic values like heart rate, blood pressure, oxygen saturation and so on). In particular, the respiratory values may include at least one of respiratory data, especially respiratory frequency, an exhalation or inhalation flow or an inhalation volume. Moreover, the second configuration data may comprise threshold values with regard to a visual/optical feedback indicator as to the proper usage ("usage support") of the spirometer system 50 and/or the respiratory gas analysis system 60 and/or with regard to proper diagnosis data. For example, a red/yellow/green feedback indication may be provided. The respective threshold values (nominal values, target values) may be appropriately set by the evaluation unit 23 of the control device 20 in dependence of the prescribed therapy protocol, for example in dependence of personal data. Such (user-specific) nominal values may indicate a number of diagnosis measurements within a prescribed time period (for example, in order to perform one spirometry measurement per week, otherwise a reminder message or warning message is triggered by the evaluation unit). Further, the setting of appropriate threshold values and/or the selection of suitable diagnosis data (for example, with regard to a specific series of diagnosis devices, such as spirometer of series A, B, C or the like) may be performed automatically, for example based on corresponding settings as defined in a database or are provided by a physician, a caregiver, hospital, pharmacist, therapist and/or health insurance. As such, the evaluation unit 23 also generates diagnosis-related real-time feedback data.

The communication unit 21 of the control device 20 may send the generated second configuration data via a (second) wireless connection to the spirometer system 50 and/or the respiratory gas analysis system 60. This second wireless communication connection is established in the same manner as the above described wireless communication connection between the control device 20 and the aerosol nebulizer system 30. Further, the communication unit 21 of the control device 20 may receive additional sensor data (i.e. respiratory values and/or non-respiratory values) that are acquired by the spirometer system 50 and/or the respiratory gas analysis system 60, in response to the second configuration data. Here, the additional sensor data may indicate the state of the respiratory tract and/or the state or function of the lung of the patient and/or a composition of the respiratory gas. In addition, or alternatively, the additional sensor data may indicate the heart rate, blood pressure and/or oxygen saturation of the user/patient, for example during the inhalation of the nebulized liquid or at a specific time point after the inhalation of the nebulized liquid.

Moreover, the additional sensor data may include spirometry values with regard to at least one of, for example: Vital Capacity (VC), Forced Vital Capacity (FVC), Total Lung Capacity (TLC), Total Capacity (TC), Inspiratory Vital Capacity (FVC), Tidal Volume (TV, or AZV), Forced Expiratory Volume in one second (FEV1), Relative Capacity of one second (FEV1/FVC), (FEV0.5 for children, FEV0.75, FEV1, FEV3, FEV6 for COPD), Maximal Expiratory Flow by 25% (FEF25) by 50% FVC (FEF50), and by 75% FVC (FEF75), further FEV0.5/FVC, FEV0.75/FVC, FEV1/FVC, FEV3/FVC, FEV6/FVC, Forced Inspiratory Vital Capacity (FIVC), FIV1, FIV1/FIVC, Peak Inspiratory Flow (PIF), Forced Expiratory Time (FET), Maximal Expiratory Pressure (MEP), Peakflow (PEF), "Z-Score"=(y−Y)/RSD, i.e. the difference between observed (y) and predicted (Y) value divided by the residual standard deviation (RSD) about the mean predicted value used as evaluation assistant, history of measurements or change of measurements as rating or evaluation, for example as an indicator for worsening or bettering of the disease as well as intelligent prediction as to the course of disease and/or patient compliance/acceptance (in the best case prediction of exacerbations), blood values, such as i.e. oxygen saturation ($O_2$), pulse, temperature, inflammatory values/markers (i.e.: White blood cells (WBCs), also called leukocytes or leucocytes, C-reactive protein—CRP, α1-Acid glycoprotein, haptoglobin, coeruloplasmin and fibrinogen, as well as interleukins—IL, i.e. IL1, up to IL31, i.e. IL6 for liver as well as IL4, IL5, IL9 and IL13 for asthma and their anti-blockers for a treatment procedure), cough monitor values (i.e. cough frequency), and/or exhalation values (for example, exacerbations counter/marker, and/or gas values, like oxygen—$O_2$, Fractionized Exhaled Nitrogen Oxide—"FENO", Nitric Oxides—"$NO_x$", Carbon Dioxide—"$CO_2$", Interleukins—"IL" see above, and/or inert gas fractions (i.e. helium [He], neon [Ne], argon [Ar], krypton [Kr], xenon [Xe], and the radioactive radon [Rn]).

More values and parameter, like FEV1, inflammatory values/markers ranges (value <26 ppb [parts per billion] =healthy), are defined i.e. by the ATS, ERS, ISAM, and GINA (abbreviation explanation above).

The usage of the aerosol nebulizer system and/or the spirometer system 50 and/or the respiratory gas analysis system 60 may be recorded and corresponding sensor data (as described above) may be transmitted to the control device 20. Here, the control device 20 may be a smart device such as a smartphone, a tablet computer, a wearable device or the like (see above), which store a corresponding application (i.e. an APP or mobile APP) to support and augment the functionality of the aerosol nebulizer and/or the spirometer and/or the respiratory gas analysis. By tethering the aerosol nebulizer, spirometer, and/or gas analysis device to the control device (via the APP), the adherence to a therapy protocol, the support of the therapy protocol, and the therapy protocol itself may be improved, for example based on the utilization, diagnosis, therapy, training, service, and the like.

The measuring signals of the respective additional sensor units may be processed (as described above) to generate additional sensor data, which may be subsequently evaluated, presented, and assessed by the control device 20, in combination or separately from the sensor data from the aerosol nebulizer system.

The sensor data control unit 22 of the control device 20 may be further configured to trigger (e.g. via a configuration data signaling/indication) also a selection of additional sensor data of the additional sensor units which is to be transmitted wirelessly from the spirometer system 50 and/or the respiratory analysis system 60 to the control device. Also the selected additional sensor data may be required for providing a real-time feedback at the control device 20. Such a real-time feedback may include running a simulation, for example a deposition simulation. Such a deposition simulation may be based on an empirical, a deterministic, and/or stochastic computational Fluid-Particle Dynamics (CFPD) model, such as described in Isaacs et al., CRCnetBASE, CiteSeerX, the Hofmann deposition model (Hofmann W., Koblinger L. [1992] Monte-Carlo modeling of aerosol deposition in human lungs. Part III. Comparison with experimental data., J. Aerosol Med. 23, 51-63), ICRP (International Commission on Radiological Protection) Publication 66 (Human Respiratory Tract Model for Radiological Protection, Ann. ICRP 24 [1-3, 1994], Mr. Dr. Rainer Koebrich PhD Program (Aerosol Bolus Calculation inspired from ICRP Publication 66), Analysis of human lung morphometric data for stochastic aerosol deposition calculations (Koblinger L., Physics in Medicine and Biology, Volume 30, Number 6), or the like.

Figure 5A:
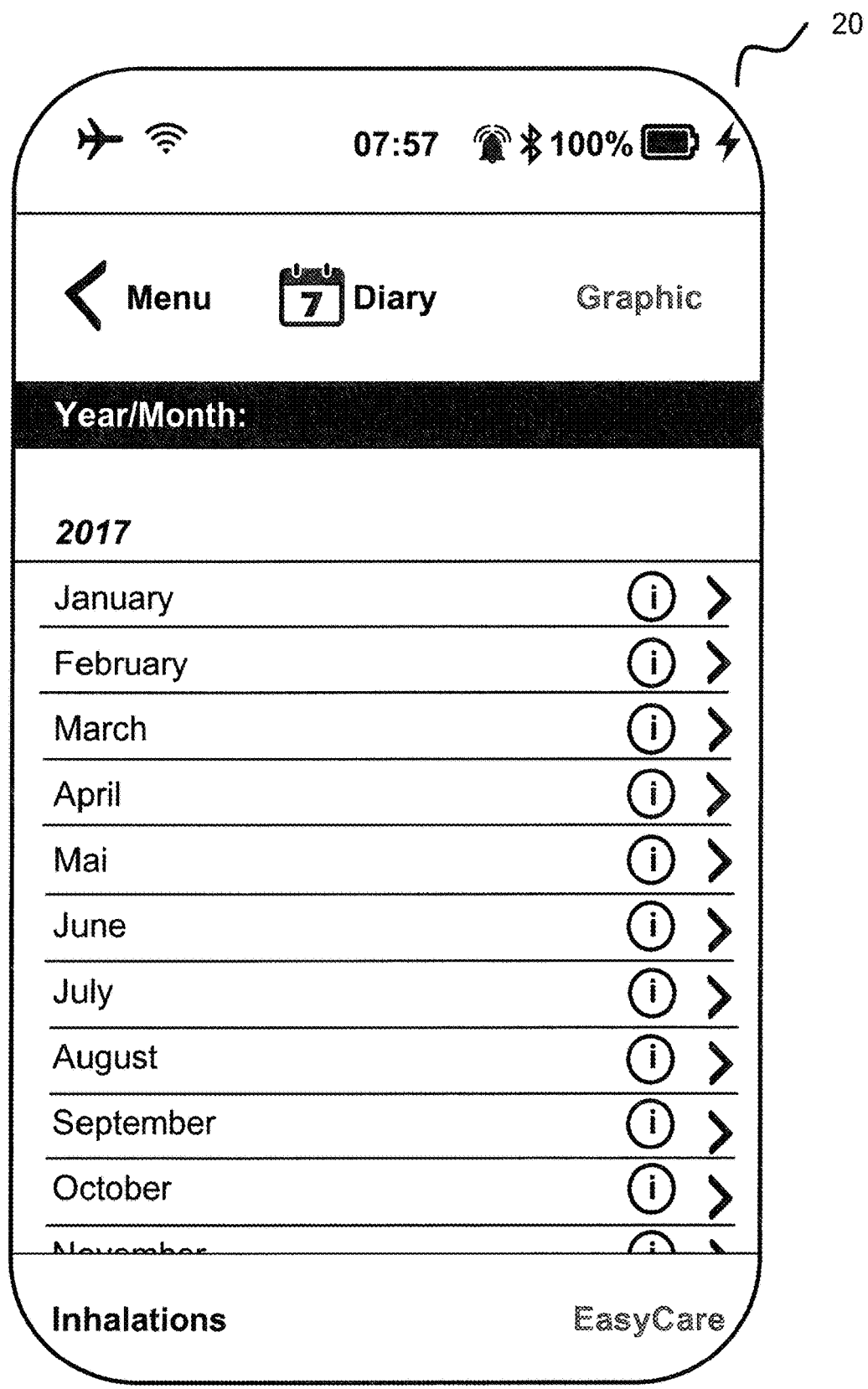
FIG. 5A-5E show respective schematic illustrations with regard to the patient training and support at the control device according to an embodiment.
Figure 5B:
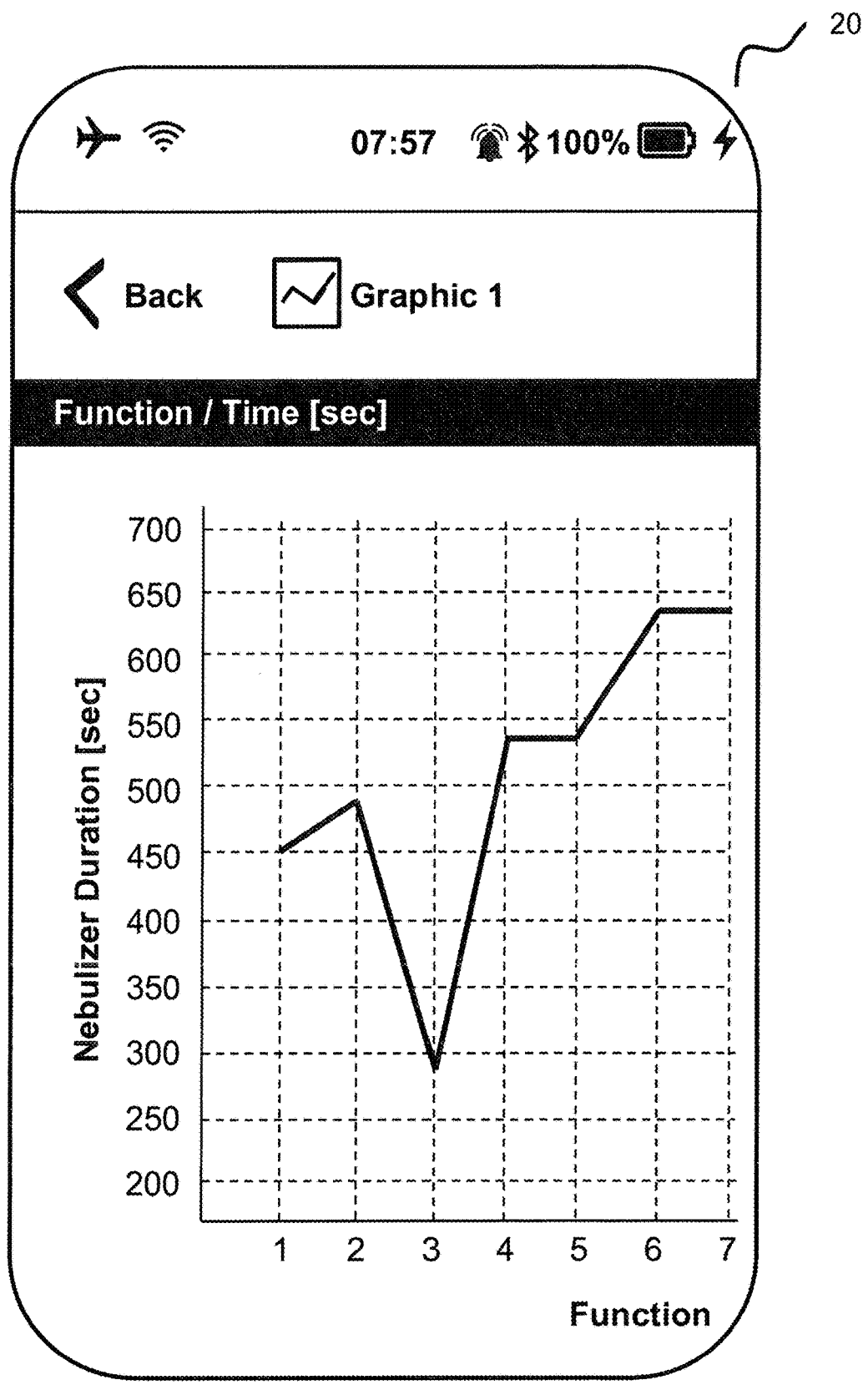
Figure 5C:
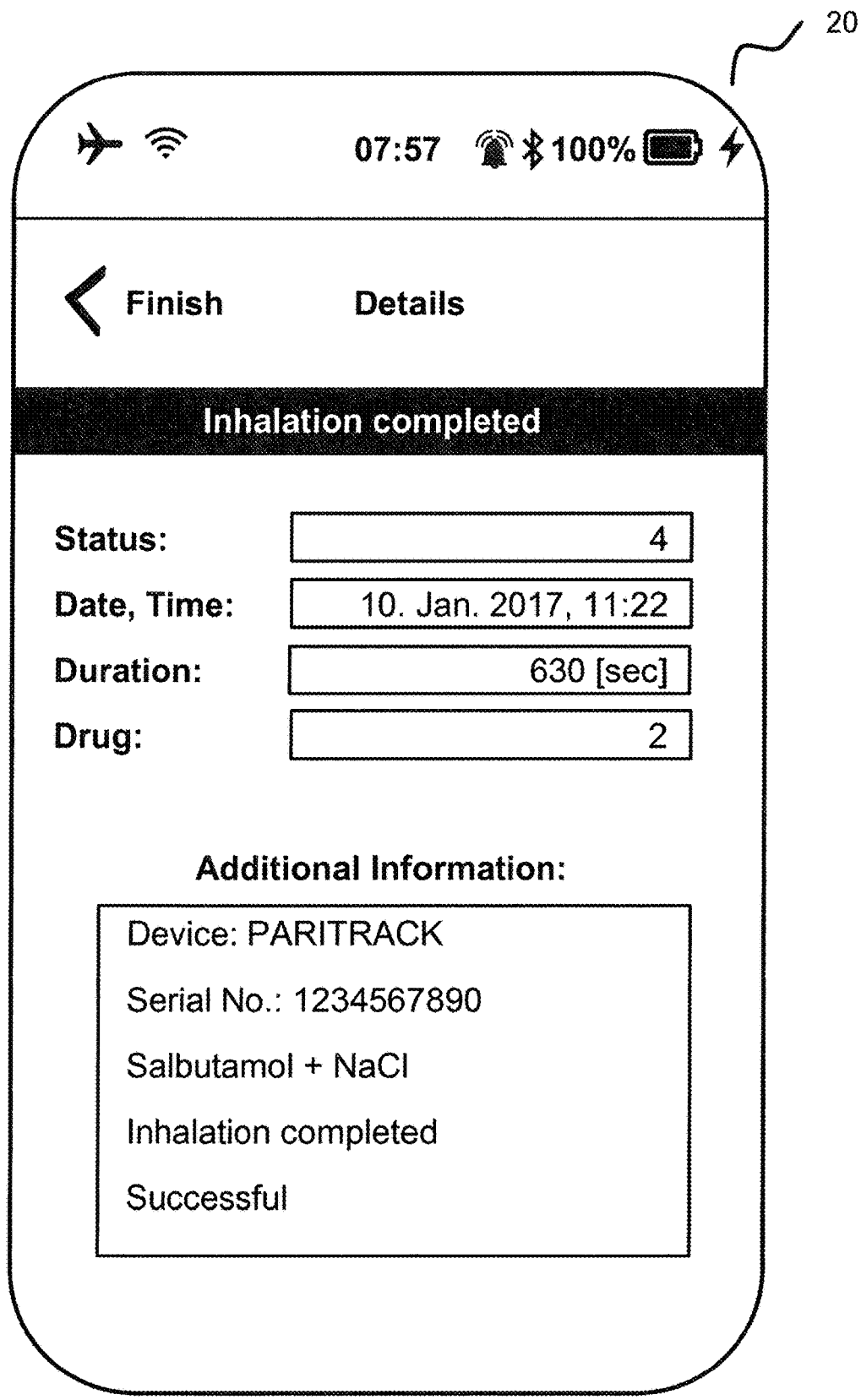
Figure 5D:
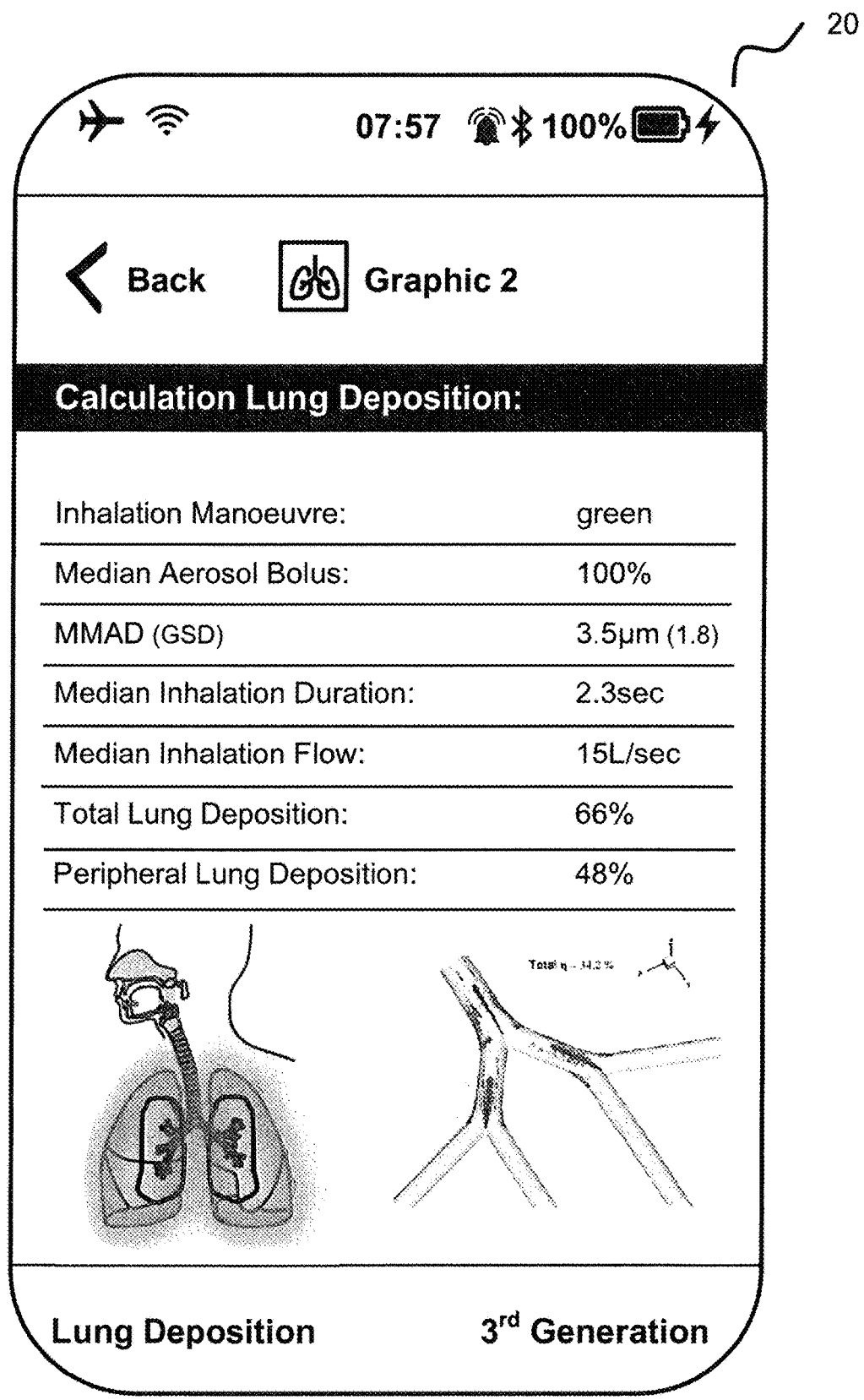

Such a deposition simulation allows for a simultaneous (real-time) indicating/displaying, at a display FIG. 5D of the control device 20, of the deposition of the aerosolized liquid within the lungs of the user. In order to provide such a real-time feedback at the control device 20, corresponding input parameter(s) (in the form of relevant (prioritized) sensor data) to the simulation are required in real time, and therefore the selection and transmission of such relevant sensor data is triggered by the sensor data control unit 22. Here, the sensor data control unit 22 may also be configured to select an operation mode (power mode switching, data mode switching), as described above, for one or more of the additional sensor units.

The feedback may be initiated when the user/patient starts using the spirometer system for a measurement, and the spirometer system sends a corresponding message to the control device 20. Similarly, the feedback may be initiated when the user/patient starts using the aerosol nebulizer system or the respiratory gas analysis system. As such, the control device 20 is provided with a corresponding notification when one of the systems is used, and changes into the respective feedback content. The feedback may then provide instructions to proper conducting of the measurements and/ or a proper handling of the respective systems. To further support the feedback, for example the cystic fibrosis animation "Patchie", a children therapy App from "Birds and Trees" (http://patchieworld.com/), or a spirometer animation like SpiroSence 360° from PARI GmbH for displaying an elephant sucking water from a bucket and spray the water over flowers (sprinkler system), or displaying different high flying balloons (J-Scope, Jager, Viasys, CareFusion), or displaying skating children on a road (Portable Spirometer, MicroLab™ Spirometer BD, CareFusion), or displaying the well-known flickering and disappearing candle lights (Koko Spirometers, nSpire Health, Viasys, CareFusion), or another "game", gamification, and/or bonus system may be used.

According to a further embodiment, the evaluation unit 23 of the control device 20 may further determine whether or not a user/patient uses the aerosol nebulizer system 30 and/or the spirometer system 50 and/or the respiratory gas analysis system 60 according to a predetermined therapy and diagnostic protocol. For example, a respective usage time and date, usage duration, usage condition (whether or not to appropriately acquire sensor data), as derivable from the acquired sensor data, may be compared with the predetermined therapy and diagnostic protocol. For example, the predetermined therapy and diagnostic protocol may indicate to conduct a spirometry measurement after a first specific number of aerosol inhalations, and to conduct a respiratory gas analysis measurement after a different, second number of aerosol inhalations. As such, by evaluating the relative occurrence of the spirometry measurement and/or gas analysis measurements with regard to the aerosol inhalations, the evaluation unit 23 may monitor the proper adherence to the therapy and diagnosis protocol.

The evaluation unit 23 may further be configured to use the sensor data of the sensor units and/or the additional sensor data of the additional sensor units to determine an adherence to the predetermined therapy and diagnostic protocol, preferably in real-time. The protocol may be defined by a physician and may subsequently be stored in a central server. The control device 20 may access the central server for the purpose of downloading the protocol. The control device may implement the protocol, for example in connection with implementing a corresponding calendar function which reminds the user/patient in case an aerosol medication inhalation and/or a spirometry measurement and/or a gas analysis measurement event is approaching.

Here, the sensor data may additionally refer to the number of times that an emergency medication has been applied (user selects which medication is used, automatic determination of the used medication as described above); respiratory flow measurements to determine the number of inhalations, an inhalation flow, an inhalation volume and the like; acoustic measurements for coughing detection, acoustic measurements during usage of the aerosol nebulizer and/or the spirometer; temperature measurement to determine fever; optical measurements; usage of an orientation sensor. Based on the above, the adherence determination may be performed in real-time and may, in particular, include one or more of:

a comparison of actual treatment and/or diagnostic intervals with the predetermined therapy and diagnostic protocol;

a comparison of actual treatment durations with the predetermined therapy protocol;

a comparison of an actual inhalation/exhalation pattern of the user with an inhalation/exhalation pattern as defined by the predetermined therapy and diagnostic protocol;

a determination of an actual aerosol delivered dose and/or deposition in the lungs of the user;

a determination of environmental factors; and/or a prediction of an imminent exacerbation of the user.

Here, the determination of environmental factors may include acquiring data as to pollen count, weather, sudden change in weather, temperature, humidity, infection areas, which may be determined based on the current position of the control device 20 (based on GPS, Galileo, Glonass, map data, telephone data, telephone net points, WiFi points or the like) and thus acquired from one or more corresponding databases. As such, the prescribed therapy and diagnostic protocol may be advantageously adapted by the control device to sudden changes in the environment, for example by adapting the frequency of spirometry measurements. In addition, the determined environmental factors may be considered in the context of the determination of the aerosol to be deposited in the lungs. The adherence to or the adaptation of the therapy and diagnostic protocol may be indicated at the control device 20, for example in the form of a visual, audible, and/or haptic indication.

Based on a combination of different sensor data (e.g. spirometer usage and aerosol nebulizer usage) together with environmental factors (e.g. pollen flight data) as well as user-specific data, the evaluation unit 23 may thus determine a particular correlation between the sensor data, factors, and user-specific data in order to predict an imminent exacerbation of the user. The arithmetic logic for the respective evaluations, correlations, and predictions may be integrated in the control device (which is configured by the APP), and may thus be regularly updated.

In a further embodiment the evaluation unit 23 of the control device 20 may be further operationally connected with a user recognition unit. Here, such a user recognition unit may be provided at the aerosol nebulizer system 30 and/or at the spirometer system 50 and/or at the respiratory gas analysis system 60, and/or at the control device 20. The patient/user recognition may be provided by a name and password, a code (for example a bar code, defining a device information which may be used when accessing a data base), smartcard, facial recognition, fingerprint, iris scan, special characteristics measured by the sensor units to further identify the user/patient (such as a sweat test, temperature indicating fever, or the like). In addition, the user recognition may also be achieved via receiving identification data from another medical device (hearing aid device, cardiac pacemaker, an insulin pump) or a vehicle which itself is provided with a capability to scan and recognize a user or driver.

The evaluation unit 23 may thus determine the patient/user that uses the respective devices and/or systems, and the corresponding systems/devices may allow proper operation only for recognized users. In addition, such a patient/user recognition process may allow aerosol generation only when a first pre-determined patient (e.g. a child) is identified as using the aerosol generator while a second pre-determined user (e.g. a parent, caregiver, physician) uses the control device 20 for supervising a proper adherence. As such, the user recognition may go beyond recognition of a single user to the recognition of (at least) two users simultaneously, which may be appropriately used to allow operation of the aerosol nebulizer or the spirometer or the gas analysis system while (parental, or the like) supervision occurs at the control device.

In a further embodiment the evaluation unit 23 of the control device 20 may be further configured to generate an emergency call function based on the evaluation of the sensor data and/or the additional sensor data. Such an emergency call to an emergency center such as an hospital, a call center, or the like may be triggered automatically by the evaluation unit 23 (for example when the evaluation unit 23 determines an acute shortness of breath, an imminent exacerbation of the user, or the like, or it may be triggered by the user). In the latter case, such an emergency call may be triggered by the user simply by operating a single button. Advantageously, operating a single button may involve generating an automated emergency message so that the user/patient itself does not have to talk to the hospital. Such functionality is of particular usefulness in cases when the health state of the user/patient does not allow a direct communication process. In addition, together with the emergency message, sensor data and/or additional sensor data are included, for example for a particular period of time, such that the emergency center may immediately evaluate the health state of the patient/user, for example by the emergency unit during their way to the patient/user. As such, potentially critical time is gained.

In another embodiment, the evaluation unit 23 may be further configured to provide an indication when the user/patient deviates from the predetermined therapy and diagnostic protocol by more than a predetermined threshold. Such an indication may be one of a visual, acoustic, or haptic indication, or a combination thereof, by using the corresponding hardware components of the control device 20, such as the screen, speaker, vibrator and the like of a smartphone. Such an indication may also be transmitted to a third party such as for example physician, caregiver, therapist, health insurance, service hot line of the user/patient. Such a threshold may be determined in advance and may indicate that the user/patient deviates from a standard behavior (as defined in therapy and diagnosis protocol). Such a threshold may also be defined, for example, with regard to an acute worsening of health state, as for example a Forced Expiratory Volume in 1 second (FeV1) below 80%, 60%, 40% of the reference value, guideline, or standard value.

In this connection, the evaluation unit 23 may also determine a usage error of using the aerosol nebulizer system 30 and/or the spirometer system 50 and/or the respiratory gas analysis system 60. In addition or alternatively, the evaluation unit 23 may also determine an error condition of the aerosol nebulizer system 30 and/or the spirometer system 50 and/or the respiratory gas analysis system 60.

The usage error refers to an error in the actual user/patient usage of the aerosol nebulizer system 30 and/or the spirometer system 50 and/or the respiratory gas analysis system 60. For example, the number of inhalations, the way (how fast, how slow, duration of pause) of performing the inhalations may be correlated with the real-time feedback (deposition simulation) to determine in which area of the lung the medication is deposited. A usage error may thus be triggered if the real-time feedback determines that the medication is not deposited in the appropriate part of the lungs. The determination of a user error may also be related to determining whether or not an appropriate aerosol generator is used, determining statistical properties of the aerosol (MMD, or the like as described above), a determination as to respiratory volume, flow, gas composition, and may thus provide the user with an indication that the present usage of the aerosol nebulizer system is incorrect because the aerosol does not arrive at the appropriate deposition spots in the lungs. Conversely, the evaluation unit 23 may indicate proper usage in order to reinforce a correct usage of the aerosol nebulizer system 30 and/or the spirometer system 50 and/or the respiratory gas analysis system 60.

The error condition relates to an error condition of the respective devices, for example an incorrect assembly, a defect battery, or the like. With regard to the aerosol nebulizer system and/or the spirometer system 50 and/or the respiratory gas analysis system 60 the error condition may thus be related to determining a present charge state of the respectively used battery, determining previous charging and/or discharging cycles, and the like (as described above). Here, the evaluation unit 23 of the control device 20 may provide support as to purchasing and exchange of a replacement battery, for example when a battery fault is imminent, or support as to a timely recharging the battery. In addition, the evaluation of the charging and/or discharging cycles may be used by the evaluation unit 23 to estimate the expected lifetime of the rechargeable battery. Sensor data indicating the state of the battery is thus always transmitted to the control device, and the discharging process and the like of the battery may thus be continuously monitored by the user/patient.

Based on the determined error condition, as described above, the evaluation unit 23 may further be configured to determine whether a part of the aerosol nebulizer system 30 and/or a part of the spirometer system 50 and/or a part of the respiratory gas analysis system 60 requires maintenance or replacement. For example, the evaluation unit 23 may determine from the sensor units of the aerosol nebulizer systems that an aerosol generator membrane (mesh) is blocked, clogged or aged, that a liquid reservoir is empty or becomes empty within a short time (for example a predetermined number of days), that the aerosol generator generates an aerosol having inappropriate characteristics or statistical properties, and the like, and thus determines that a membrane has to be replaced, a liquid has to be refilled, that the aerosol generator requires maintenance, respectively. In addition, when the particular type of aerosol generator is identified in connection with a particular medication used for this type of aerosol generator, the nebulization time may be evaluated, from which it may be derived whether a cleaning of the aerosol generator or a replacement is necessary. This may be combined with providing guidance to the user at the control device as to a proper cleaning or requesting a replacement aerosol generator. In addition, the evaluation unit 23 may determine whether a battery has to be replaced or has to be recharged. In such a case, the evaluation unit 23 may accordingly use a push notification or the like to inform the user.

In addition, a sensor unit of the spirometer system may have to be exchanged after one year. Further, if a mouthpiece of the spirometer system with a filter included is old or dirty, this also needs to be replaced.

Figure 5E:
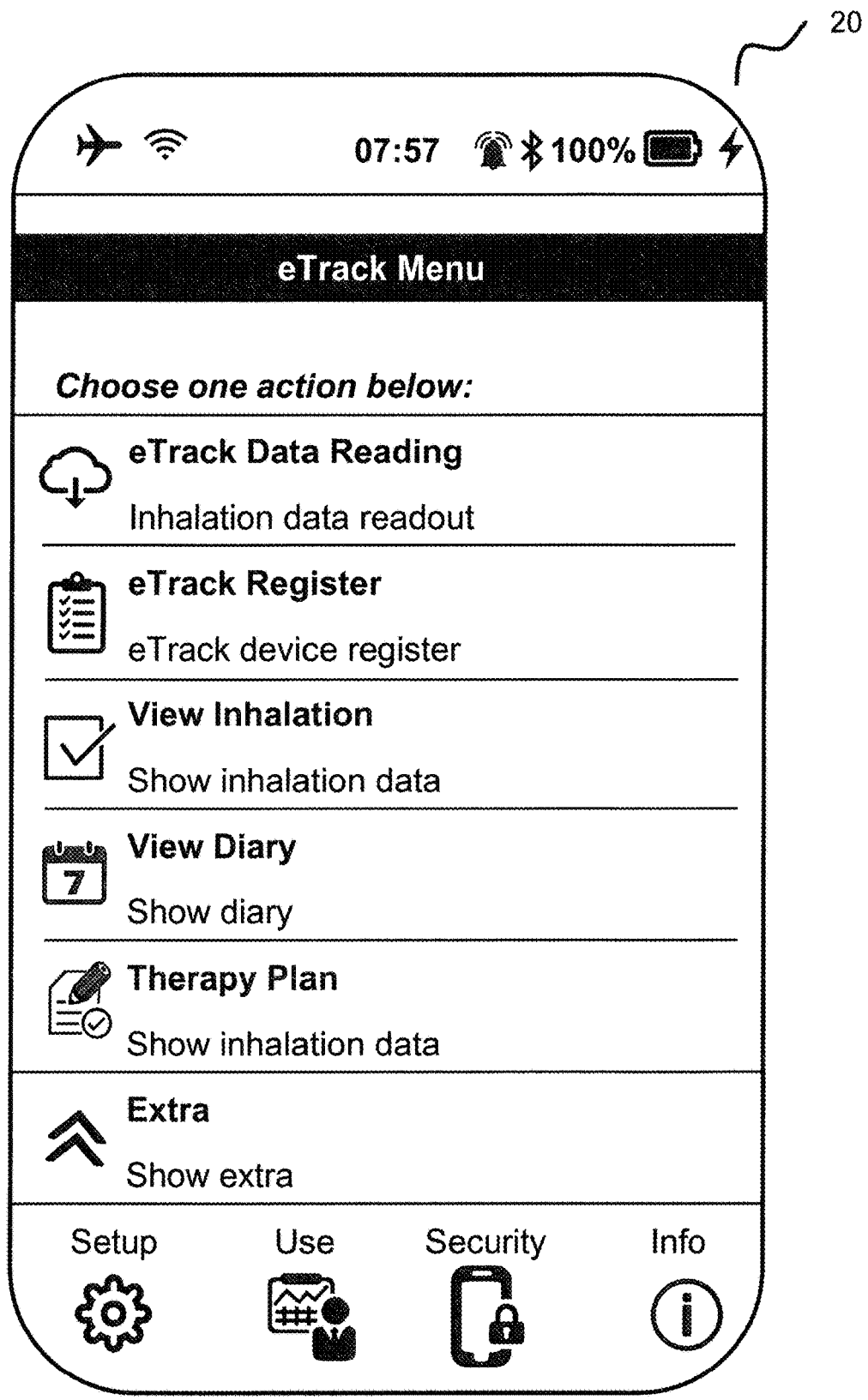

The replacement may also include a replacement service like a one buy click button in the application software program (i.e. App), such as for example the "1Click®" button (Amazon), for the aerosol generator, battery, mixing chamber, yearpack and/or further replacement parts. In a further replacement service setup this replacement order may start automatically, for example if a service contract is in place and/or a service hot line may be contacted, as well as the caregiver, replacement service, and/or device manufacturer. The contact could be done for example via email, telephone, mobile, smartphone, tablet, notebook, netbook, PC, and/or HUB.

In addition, such a determination may also be based on a determination of nebulizer usage time for a particular medication, on an evaluation of usage duration, usage frequency, and/or cleaning behavior of the aerosol generator, the spirometer, and/or respiratory gas analysis system.

In addition, when an usage error and/or an error condition is determined, and/or when a part of the aerosol nebulizer system 30 and/or the spirometer system 50 and/or the respiratory gas analysis system 60 requires maintenance or replacement, then the evaluation unit 23 of the control device may initiate to transmit a notification message to a caregiver, to a call center, and/or to a physician, on top of an indication as provided at the control device 20. As such, an appropriate handling of maintenance/replacement needs may also be supported by the receiving unit of such a notification. As explained above, the control device may also be configured to directly order such replacement parts.

Further, in another embodiment the evaluation unit 23 may adapt the configuration data of the aerosol nebulizer system 30 and/or the spirometer system 50 and/or the respiratory gas analysis system 60. In particular, such configuration data may be adapted with regard to user-specific thresholds and/or parameters which are used for visual, audible, and/or haptic indications at the respective systems. Such user-specific thresholds and/or parameters may be appropriately updated based on the real-time feedback, as described above. The configuration data may also be adapted with regard to the usage of another aerosol generator type, or the like. Such user-specific thresholds may also include user-specific ranges to implement a "traffic light" indication. In particular, such configuration data may also include parameters for the proper operation of new aerosol generator types and the like. The aerosol nebulizer system 30 and/or the spirometer system 50 and/or the respiratory gas analysis system 60 may thus be personalized by the control device 20.

The indication and/or warning may support a training of the patient/user towards an optimization of the breathing and/or inhalation maneuver. Such training may further include providing time-dependent threshold values which are suitably adapted, i.e. reduced, as the training progresses and the patient/user develops breathing and/or inhalation patterns that exhibit an improved adherence to the optimal breathing and/or inhalation maneuver. Such training may further include providing acoustic and/or visual clues to the patient/user as to respective timings to start inhaling and/or respective timings to end inhaling.

The sensor data that have been acquired by the control device 20 in conjunction with the aerosol nebulizer system 30 and/or the spirometer system 50 and/or the respiratory gas analysis system 60 may be stored, managed or shared in a variety of options. For example, the sensor data may be locally stored in the storage unit 25 of the control device 20. On the other hand, the sensor data may be synchronized with a cloud solution or a centralized server in order to provide access by the physician as well as for example a clinic research organization (CRO), caregiver, and therapist and so on.

The control device 20 may further provide an electronic diary to the patient/user, which may be supplemented by standardized questionnaires (e.g. ACT symptom score) or other individual or general questions or possibilities for comments like special individual health-related actual happenings (e.g. acute coughing, contact to allergens like polls or pets). The control device 20 may further provide general information on use of the device and/or information on respiratory research or lung diseases and links to updated services and information in the internet linked to respiratory diseases, therapies and research.

FIG. 5A-5E show respective schematic illustrations (to be shown at a display unit of the control device) with regard to the patient training and support at the control device according to an embodiment.

In particular, FIG. 5A shows a schematic illustration of an electronic diary to the patient/user with regard to specific months, days, and times of a day. When entering a specific day in the electronic diary, the acquired therapy-related data may be accessed and visualized, for example the amount of inhalation time as illustrated in FIG. 5B. Additional information with regard to individual inhalations may also be indicated, as shown in FIG. 5C which indicates that an inhalation process was successfully conducted (status 4), at a particular date and time, with the duration of the inhalation process, and an indication of the particular medication used.

It is noted that different status parameters may be used, in particular an error status such as no inhalation device connected, no medication present, battery empty, timeout, termination by the user, and the like. Further FIG. 5D schematically illustrates the result of a deposition simulation which indicates to the user in real-time at least a part of a schematic representation of a lung together with an indication as to deposition sites of the inhaled aerosol. The lung deposition may be displayed for the total lung, central lung, and/or peripheral lung as well as for e.g. the $3^{rd}$ Generation of the respiratory airway branches and so on. Further may be displayed the median particle size (MMAD) and geometric standard deviation (GSD) as well as the duration and/or the ratio of the inhalation phase or the aerosol bolus in relation to the total duration of the inhalation maneuvers. Further, FIG. 5E schematically illustrates selection options for the patient training and support at the control device. In particular, FIG. 5E shows that a user may select between inhalation data read out, viewing the inhalation data (including the deposition simulation or behavior, as described in FIG. 5D), registering the aerosol nebulizer system, electronic diary, and handling (editing) the protocol. Needless to say, the patient training and support may also provide corresponding functionality with regard to the spirometer system and/or the respiratory gas analysis system.

According to another embodiment, a computer program is provided that includes instructions which, when executed on one or a plurality of processors of a computer, cause the processor or the plurality of data processors to implement the control device 20 as described above.

Figure 6:
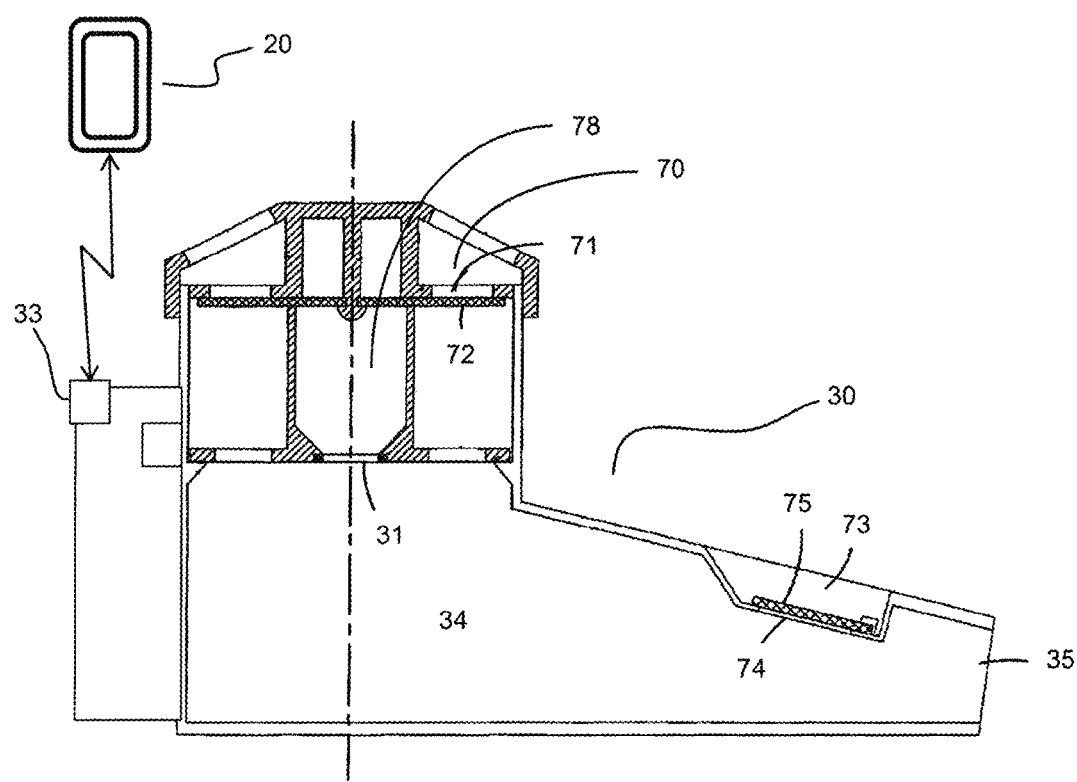
FIG. 6 shows a schematic illustration of a mixing chamber with inhalation valve and exhalation valve for an aerosol nebulizer system according to an embodiment.

FIG. 6 shows a control device 20 as described above in combination and communication interaction with an aerosol nebulizer system 30 according to another embodiment. In the following, the particular structure of the aerosol nebulizer system 30 with regard to a mixing chamber 34 will be described. Of course, the above-described sensor units are also provided for the aerosol nebulizer system 30 according to FIG. 6. In addition to the above-described sensor units, a sensor unit may be provided with regard to (e.g., in proximity to) an inhalation valve 70 and/or an exhalation valve 73 (to be described below).

This further embodiment of the invention may involve an aerosol nebulizer system 30 having both an aerosol generator 31 and a mixing chamber 34. The aerosol generator 31 includes a liquid storage container 78 for e.g. a liquid and/or a liquid medicament. This liquid medicament can be a liquid and/or drug formulation consisting a solution, suspension or emulsion that contains the medicament of interest. In a preferred embodiment, the liquid medicament is an active agent or active pharmaceutical ingredient that is formulated in a solution, a suspension or an emulsion. The aerosol generator also includes a perforated membrane that is connected on one side to the liquid storage container such that a liquid contained in the liquid storage container will come into contact with one side of the perforated membrane (diaphragm, mesh). The membrane is connected to a vibration generator that can vibrate the membrane so that a liquid in the liquid storage container can be dispensed or dosed for atomization through openings present in the membrane and enter the mixing chamber. The mixing chamber has an inhalation valve 70 that allows ambient air to flow into the mixing chamber 34 during an inhalation phase while preventing aerosol from escaping during an exhalation phase. The mixing chamber 34 also has an exhalation valve 73 that allows discharge of the patient's respiratory air during the exhalation phase while preventing an inflow of ambient air during the inhalation phase.

Referring to the construction illustrated in FIG. 6 as an embodiment of the present invention, the aerosol generator 31 includes a cylindrical liquid storage container 78 that is defined on one side by a membrane (one part of the aerosol generator 31) that preferably is a circular disk. A liquid (not shown) filled in the liquid storage container contacts one side of the membrane. A vibration generator, for instance a piezoelectric crystal, surrounds the membrane circumferentially such that the membrane can be vibrated by the vibration generator. This requires an electric drive circuit or the control device 20 as described above for the vibration generator. Through openings present in the membrane, the liquid adjoining one side of the membrane is atomized through to the other side of the membrane and thus is atomized into the mixing chamber 34.

The liquid storage container 78 preferably provides an entry point for the particular medicament to be dispensed. In one embodiment, the liquid storage container 78 is a liquid reservoir that is directly fitted into the aerosol nebulizer system 30. In another embodiment, the medicament is provided to the liquid storage container 78 as a metered volume from either a single dose or multi dose container. If a multi dose container is used, it is preferably equipped with a standard metering pump system as used in commercial nasal spray products.

If the liquid storage container 78 is cylindrical, it is preferred that the membrane has a circular design and the vibration generator has an annular design. The aerosol nebulizer system 30 includes an aerosol generator 31 and a mixing chamber 34 having an inhalation valve 70 and an exhalation valve 73.

Preferably, the aerosol generator 31 is arranged in a section of the mixing chamber 34 that is also of a cylindrical design. Thereby an annular gap is obtained around the aerosol generator 31 through which the ambient air can flow into the mixing chamber 34 during the inhalation phase.

A mouthpiece 35 is preferably integrally formed with the mixing chamber 34, but it also can be attached removably to the mixing chamber. A patient inhales the aerosol through the mouthpiece 35. The aerosol is generated by the aerosol generator 31 and is stored in the mixing chamber 34. The size and the form of the mouthpiece 35 can be chosen such that it enlarges the mixing chamber 34 and simultaneously provides for the arrangement of the exhalation valve 73. The exhalation valve is preferably located adjacent to the opening of the mouthpiece 35 facing the patient.

When a patient exhales into the opening of the mouthpiece 35, the exhalation valve 73 is opened so that the respiratory air of the patient is discharged into the surroundings. To this end, a valve element 75 of the exhalation valve 73 is lifted and frees the opening 74 of the exhalation valve 73. The inhalation valve 70 is closed when the patient exhales into the inhalation nebulizer, as the valve element 72 of the inhalation valve 70 closes the opening 71 of said valve.

When a patient inhales through the opening of the mouthpiece 35, the inhalation valve 70 is opened and frees the opening 71 as the valve element 72 is lifted. Thereby ambient air flows through the inhalation valve 70 and the annular gap into the mixing chamber 34 and is inhaled by the patient together with the aerosol. As aerosol has accumulated in the mixing chamber 35 during an exhalation phase, there is available to the patient an increased amount of aerosol, a so-called aerosol bolus, especially at the beginning of an inhalation phase.

In a preferred embodiment, the inhalation valve is adapted to the cylindrical form of the aerosol and the annular gap.

The flexible valve element 72 is formed as a circular disk that is attached at a centrally arranged fastening projection of a cap mounted at, e.g. screwed on, the cylindrical section of the mixing chamber 34. The cap also has a cylindrical connecting piece which, in interaction with the outer wall of the liquid storage container 78, clamps and fastens the valve element 72.

At the side of the cylinder connecting piece facing the liquid storage container 78 there is also integrally formed a first circular ring disk 72 in which the openings 71 of the inhalation valve 70 are defined. Corresponding openings are provided in the cap so that ambient air can flow through the openings 71 and the gap into the mixing chamber 34 during an inhalation process. At the front side comprising the membrane the aerosol generator 31 has a second circular ring disk with openings through which the ambient air flows during the inhalation phases. The circular ring disk rests upon a projection formed at the inner wall of the cylindrical section of the mixing chamber 34. Thus, when the cap is positioned thereupon or screwed thereon, the aerosol generator 31 and the flexible valve element 72 of the inhalation valve 70 are securely fixed.

Apart from the above described cylindrical design of the aerosol membrane generator and of a section of the mixing chamber, other substantially rotationally symmetrical designs can advantageously be used. Furthermore, the membrane of the aerosol generator can also be arranged in an inclined position whereby the spreading of the aerosol generated by the aerosol membrane generator can be influenced and thus, with regard thereto, the specific design of the mixing chamber and also of the mouthpiece can be optimized.

The mixing chamber 34 or so called inhalation chamber 34 having at least one of an inhalation valve 79 and an exhalation valve 73 in which the inhalation valve and exhalation valve may be formed as one-way valves that have openings 71, 74 with flexible membranes 72, 75 respectively. This setup of the mixing chamber 34 is shown in FIG. 6, and enhances the aerosol output, because the aerosol cloud accumulates during the exhalation phase and a concentrated aerosol bolus is delivered to the user during the inhalation phase.

As described above, an additional sensor unit may be provided with regard to (e.g., in proximity to) an inhalation valve 70 and/or an exhalation valve 73, and is thus placed at the position of the inhalation valve 70 and/or an exhalation valve 73, for example at a contact surface close to the respective valve. Such an additional sensor unit may detect, for example by an optical or acoustic detection, whether the respective valve switches in accordance with the detected breathing manoeuver. Such an additional sensor unit may detect the one-way valve closure or close-position, for example by an optical or acoustic detection, or preferred by contact detection. Therefore for example the flexible membrane and valve seat of the one-way-valve may be formed partly of an electro-conductive flexible material, which may be formed in a two-component flexible and/or inflexible material. The material may be formed in part or in total of polymer, plastic, silicon, rubber, polyurethane, polypropylene or the like material. In addition, flow turbulences, pressure differences (for example, between an interior and exterior side of the mixing chamber, or within the mixing chamber), and/or aerosol flows within the mixing chamber may be detected, and provided as respective sensor data to the control device 20. The above described sensor data control unit 22 may also trigger a selection with regard to these sensor data.

According to another embodiment, a control device is provided for controlling a spirometer system 50 as described above and/or a respiratory gas analysis system 60 as described above, where the spirometer system 50 and/or said respiratory gas analysis system 60 comprising a plurality of additional sensor units. Here, the communication unit 21 is configured to establish a wireless communication connection and to perform data transmission with the spirometer system 50 and/or the respiratory gas analysis system 60, and the sensor data control unit 22 is configured to trigger a selection of additional sensor data of the additional sensor units to be wirelessly transmitted to the control device 20. As described above, the selected additional sensor data are required for providing a real-time feedback at the control device, and the sensor data control unit 22 may control an operation mode of one or more of the additional sensor units. This operation mode may include a power mode switching and/or a data mode switching, as described above. Such a control device may also be configured to control an operation of an aerosol nebulizer system as described above.

The above respective units of the control device may thus be implemented by a respective processing unit (CPU) that includes one or a plurality of processors, a microprocessor or other processing logic that interprets and executes instructions as defined by the computer program and stored in a main memory. The main memory may include a RAM or other type of dynamic storage device that may store information and instructions for execution by the respective modules/units. For example, the evaluation unit and/or the sensor data control unit discussed above may be realized by the processing unit. The ROM may include a ROM device or another type of static storage device that may store static information and instructions for use by the processing unit.

The control device 20 may perform these operations in response to the processing unit executing software instructions contained in a computer-readable medium, such as the main memory, ROM and/or storage device. A computer-readable medium may be defined as a physical or a logical memory device. For example, a logical memory device may include memories within a single physical memory device or distributed across multiple physical memory devices. Each of the main memory, ROM and storage device may include computer-readable media with instructions as program code. The software instructions may be read into the main memory for another computer-readable medium, such as a storage device or from another device via the communication interface.

The software instructions contained in the main memory may cause the processing unit(s) including a data processor, when executed on the processing unit, to cause the data processor to perform operations or processes described herein. Alternatively, hard-wired circuitry may be used in place or in combination with the software instructions to implement processes and/or operations described herein. Thus, implementations described herein are not limited to any specific combination of hardware and software.

Further, the respective units of the control device may be implemented in hardware, software, Field Programmable Gate Arrays (FPGAs), application-specific integrated circuits (ASICs), firmware or the like.

It will be apparent to those skilled in the art that various modifications and variations can be made in the entities and methods of this invention as well as in the construction of this invention without departing from the scope of the invention.

The invention has been described in relation to particular embodiments and examples which are intended in all aspects to be illustrative rather than restrictive. Those skilled in the art will appreciate that many different combinations of hardware, software and/or firmware will be suitable for practicing the present invention.

The invention claimed is:

1. Control device for controlling an operation of an aerosol nebulizer system, said aerosol nebulizer system comprising an aerosol generator for nebulizing a liquid and a plurality of sensor units, said control device comprising:
   a communication unit, configured to establish a wireless communication connection and to perform data transmission with the aerosol nebulizer system, and
   a sensor data control unit, configured to
trigger, by transmitting an indication, a selection of sensor data related to the sensor units to be wirelessly transmitted to the control device, such that, during inhalation, only a selected and prioritized subset of sensor data are transmitted to the control device while remaining sensor data are temporarily stored at the aerosol nebulizer system for a subsequent transfer.

2. Control device according to claim 1, wherein the selected sensor data are required for providing a real-time feedback at the control device.

3. Control device according to claim 1, wherein the sensor data control unit is further configured to control an operation mode of one or more of the sensor units.

4. Control device according to claim 3, wherein the operation mode includes a power mode switching.

5. Control device according to claim 3, wherein the operation mode includes a data mode switching.

6. Control device according to claim 1, wherein the sensor units of the aerosol nebulizer system include at least two of:
   an aerosol sensor unit;
   an operation state sensor unit;
   a breathing maneuver sensor unit;
   an environmental condition sensor unit;
   a user recognition sensor unit;
   an aerosol generator identification sensor unit;
   a medication identification sensor unit;
   a medication fill level sensor unit;
   an aerosol nebulizer battery sensor unit.

7. Control device according to claim 1, wherein the control device is further configured for controlling a spirometer system and/or a respiratory gas analysis system,
   said spirometer system and/or said respiratory gas analysis system comprising a plurality of additional sensor units, wherein
   the communication unit is further configured to establish a wireless communication connection and to perform data transmission with the spirometer system and/or the respiratory gas analysis system, and
   the sensor data control unit is further configured to trigger a selection of additional sensor data of the additional sensor units to be wirelessly transmitted to the control device.

8. Control device according to claim 7, wherein the sensor data control unit is further configured to select an operation mode of one or more of the additional sensor units.

9. Control device according to claim 7, wherein the additional sensor units include at least two of:
   a lung diagnostic sensor unit;
   a breathing gas sensor unit;
   a battery sensor unit;
   a temperature sensor unit;
   a user recognition sensor unit.

10. Control device according to claim 1, further comprising an evaluation unit configured to determine whether or not a user uses the aerosol nebulizer system and/or the spirometer system and/or the respiratory gas analysis system according to a predetermined therapy and diagnostic protocol.

11. Control device according to claim 10, wherein the evaluation unit is configured to use the sensor data of the sensor units and/or the additional sensor data of the additional sensor units to determine an adherence to the predetermined therapy and/or diagnostic protocol, in particular one or more of:
    to compare actual treatment and/or diagnostic intervals with the predetermined therapy and diagnostic protocol;
    to compare actual treatment durations with the predetermined therapy protocol;
    to compare an actual inhalation/exhalation pattern of the user with an inhalation/exhalation pattern as defined by the predetermined therapy and diagnostic protocol;
    to determine an actual aerosol delivered dose and/or deposition in the lungs of the user;
    to determine environmental factors; and/or
    to predict an imminent exacerbation of the user.

12. Control device according to claim 10, wherein the evaluation unit is operationally connected to a user recognition unit.

13. Control device according to claim 10, wherein the evaluation unit is further configured to generate an emergency call or alert function based on the evaluation of the sensor data of the sensor units and/or the additional sensor data of the additional sensor units.

14. Control device according to claim 10, wherein the evaluation unit is further configured to provide an indication when the user deviates from the predetermined therapy and diagnostic protocol by more than a predetermined threshold.

15. Control device according to claim 10, wherein the evaluation unit is further configured to determine a usage error of using the aerosol nebulizer system and/or the spirometer system and/or the respiratory gas analysis system.

16. Control device according to claim 15, wherein the evaluation unit is further configured to transmit a notification message when determining a usage error, error condition, and/or when a part of the aerosol nebulizer system and/or a part of the spirometer system and/or a part of the respiratory gas analysis system requires maintenance or replacement.

17. Control device according to claim 10, wherein the evaluation unit is further configured to determine an error condition of the aerosol nebulizer system and/or the spirometer and/or the respiratory gas analysis system.

18. Control device according to claim 10, wherein the evaluation unit is further configured to determine whether a part of the aerosol nebulizer system and/or a part of the spirometer system and/or a part of the respiratory gas analysis system requires maintenance or replacement.

19. Control device according to claim 1, wherein the control device further adapts configuration data of the aerosol nebulizer system and/or the spirometer system and/or the respiratory gas analysis system, in particular
    to user-specifically adapt thresholds and/or parameters used for a visual, audio, and/or haptic indication.

20. Control device according to claim 1, wherein the wireless connection communication connection is one of a Bluetooth connection, a Bluetooth Low Energy connection, a near field connection, a WiFi or WLAN connection, an infrared connection, or a radio connection.

21. Control device according to claim 1, wherein the control device is one of a smartphone, a tablet or another portable or wearable device.

22. Control device according to claim 1, wherein the processing unit of the aerosol nebulizer system includes a data filtering and/or data logic to reduce the data amount to be transmitted to the control device.

23. Control device according to claim 1, wherein the aerosol nebulizer system is further provided with
- a mixing chamber into which the aerosol generator releases the aerosol;
- an inhalation valve; and
- an exhalation valve.

24. Control device according to claim 1, wherein the aerosol nebulizer system is further provided with
- a mixing chamber into which the aerosol generator releases the aerosol;
- an inhalation valve that is opened to allow an inflow of ambient air into the mixing chamber during an inhalation phase and is closed to prevent escape of the aerosol from the mixing chamber during an exhalation phase; and
- an exhalation valve that is opened to allow the discharge of the respiratory air of a patient into the surroundings during the exhalation phase and is closed to prevent the inflow of ambient air during the inhalation phase.

25. A computer program, comprising instructions which, when executed on at least one processor of a computer, cause the at least one processor to function as a control device according to claim 1.

26. A computer-readable storage medium, having stored thereon a computer program according to claim 25.

27. A carrier containing the computer program according to claim 25, wherein the carrier is one of an electrical signal, optical signal, radio signal, or computer-readable storage medium.

* * * * *